US009382279B2

(12) United States Patent
Schomaker et al.

(10) Patent No.: US 9,382,279 B2
(45) Date of Patent: Jul. 5, 2016

(54) COPPER CATALYZED HALOGENATON AND REACTION PRODUCTS

(71) Applicant: Wisconsin Alumni Research Foundation, Madison, WI (US)

(72) Inventors: Jennifer Marie Schomaker, Madison, WI (US); Robert David Grigg, Madison, WI (US); Ryan Jon Van Hoveln, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/305,114

(22) Filed: Jun. 16, 2014

(65) Prior Publication Data

US 2014/0371480 A1 Dec. 18, 2014

Related U.S. Application Data

(60) Provisional application No. 61/835,410, filed on Jun. 14, 2013.

(51) Int. Cl.
| | |
|---|---|
| *C07F 9/6568* | (2006.01) |
| *C07F 9/50* | (2006.01) |
| *C07F 9/655* | (2006.01) |
| *C07F 5/02* | (2006.01) |
| *C07F 17/02* | (2006.01) |
| *C07B 37/04* | (2006.01) |

(52) U.S. Cl.
CPC ............. *C07F 9/65683* (2013.01); *C07B 37/04* (2013.01); *C07F 5/025* (2013.01); *C07F 9/5027* (2013.01); *C07F 9/65522* (2013.01); *C07F 9/65527* (2013.01); *C07F 17/02* (2013.01)

(58) Field of Classification Search
None
See application file for complete search history.

(56) References Cited

U.S. PATENT DOCUMENTS

| | | | |
|---|---|---|---|
| 6,451,937 | B1 | 9/2002 | Hartwig et al. |
| 6,624,320 | B2 | 9/2003 | Matsumura et al. |
| 2005/0124808 | A1 | 6/2005 | Miller |
| 2006/0205966 | A1 | 9/2006 | Westcott et al. |

OTHER PUBLICATIONS

*Advanced Organic Chemistry, Part B: Reactions and Synthesis, Second Edition*, Cary and Sundberg (1983) (Complete Book—Copy not provided).
Becke, A. D., Densityfunctional thermochemistry. III. The role of exact exchange, *J. Chem. Phys*. 1993, 98, 5648-5652.
Binning et al., Compact Contracted Basis Sets for Third-Row Atoms: Ga-KR, *J. Comp. Chem*. 1990, 11, 1206-1216.
*Compendium of Organic Synthetic Methods* (John Wiley & Sons, New York), vol. 1, Ian T. Harrison and Shuyen Harrison, 1971; vol. 2, Ian T. Harrison and Shuyen Harrison, 1974; vol. 3, Louis S. Hegedus and Leroy Wade, 1977; vol. 4, Leroy G. Wade, Jr., 1980; vol. 5, Leroy G. Wade, Jr., 1984; and vol. 6 (Complete Book—Copy not provided).
*Comprehensive Organic Synthesis. Selectivity, Strategy & Efficiency in Modern Organic Chemistry*. In 9 Volumes, Barry M. Trost, Editor-in-Chief (Pergamon Press, New York, 1993 printing (Complete Book—Copy not provided).
*Comprehensive Organic Transformations*, Larock, R.C., 2$^{nd}$ Ed., John Wiley & Sons, New York (1999) (Complete Book—Copy not provided).
Curtiss et al., Extension of Gaussian2 theory to molecules containing thirdrow atoms Ga—Kr, *J. Chem. Phys*. 1995, 103, 6104-6113.
Greene, T.W., *Protecting Groups In Organic Synthesis*; Wiley: New York, 1981 (Complete Book—Copy not provided).
Glendening et al., NBO 6.0 Program Manual, (Theoretical Chemistry Institute, University of Wisconsin, Madison, WI, 2013); http://nbo6.chem.wisc.edu/).
Grigg et al., Copper-Catalyzed Recycling of Halogen Activating Groups via 1,3-Halogen Migration, *J. Am. Chem. Soc*. 2012, 134, 16131.
Grigg et al., Activating Group Recycling: A Fresh Approach to Arene Functionalization, *Synlett*, 2013, 24, 401.
Huffman et al., Lithium Alkoxides of Cinchona Alkaloids as Chiral Controllers for Enantioselective Acetylide Addition to Cyclic *N*-Acyl Ketimines, *J. Org. Chem*. 1995, 60, 1590-1594.
Kocienski, Philip J.; *Protecting Groups* (Georg Thieme Verlag Stuttgart, New York, 1994) (Complete Book—Copy not provided).
Krishnan et al., Selfconsistent molecular orbital methods. XX. A basis set for correlated wave functions, *The Journal of Chemical Physics* (1980) 72, 650.
*March'S Advanced Organic Chemistry: Reactions, Mechanisms, and Structure*, 5$^{th}$ Ed., by M.B. Smith and J. Mar. (John Wiley & Sons, New York, 2001) (Complete Book—Copy not provided).
McGrath et al., Extension of Gaussian1 (G1) theory to bromine containing molecules, *J. Chem. Phys*. 1991, 94, 511-516.
McLean et al., Contracted Gaussian basis sets for molecular calculations. I. Second row atoms, Z=11-18, *J. Chem. Phys*. 1980, 72, 5639-5648.
*Protecting Groups in Organic Synthesis, Second Edition*, Greene, T.W., and Wutz, P.G.M., John Wiley & Sons, New York (Complete Book—Copy not provided).
Tucker et al., Synthesis of a Series of 4-(Arylethynyl)-6-chloro-4-cyclopropyl- 3,4-dihydroqui8nazolin-2(1*H*)-ones as Novel Non-nucleoside HIV-1 Reverse Transcriptase Inhibitors, *J. Med. Chem*. 1994, 37, 2437-2444.

*Primary Examiner* — Samantha Shterengarts
(74) *Attorney, Agent, or Firm* — Joseph T. Leone, Esq.; DeWitt Ross & Stevens S.C.

(57) ABSTRACT

A Cu(I)-catalyzed 1,3-halogen migration reaction effectively recycles an activating group by transferring a halogen from an sp$^2$ to a benzylic carbon with good enantioselectivity and concomitant borylation of the Ar-halo bond. The resulting enantio-enriched benzyl halide can be reacted in the same vessel under a variety of conditions to form an additional carbon-heteroatom or carbon-carbon bond while maintaining high ee. The reaction can be used to efficiently prepare novel compounds and intermediates for the preparation of therapeutics and ligands for catalysis.

29 Claims, No Drawings

COPPER CATALYZED HALOGENATON AND REACTION PRODUCTS

CROSS-REFERENCE TO RELATED APPLICATIONS

Priority is hereby claimed to provisional application Ser. No. 61/835,410, filed Jun. 14, 2013, which is incorporated herein by reference.

BACKGROUND OF THE INVENTION

Alkyl, benzylic and allylic bromides are fundamental building blocks that can be used in a wide range of transformations of both practical and historical significance. In spite of this, setting the stereochemistry of a halogen-bearing carbon remains challenging. A great deal of research has focused on asymmetric α-halogenation of carbonyls and amino-halogenations of olefins. However, these techniques rely heavily on stoichiometric sources of chirality in the form of chiral auxiliaries or chiral brominating agents. To date, the catalytic systems that set the stereochemistry of a halogen-carbon bond, with the exception of halolactonizations, are sparse. Furthermore, to the best of our knowledge, enantioselective hydrobrominations of olefins have not been reported. Accordingly, new methods for the efficient and enantioselective hydrobrominations of olefins would provide more efficient and economical access to a variety of important synthetic building blocks, including drug intermediates and chiral phosphines.

Additionally, chiral, non-racemic phosphines are crucial components in a multitude of important enantioselective transformations, including asymmetric Diels-Alder reactions, hydroformylations, aldol reactions, aminations, hydrogenations, hydrosilylations, conjugate additions and other carbon-carbon bond formations. However, the syntheses of enantioselective phosphine ligands often require multiple steps, including chiral resolutions to separate enantiomers. The lack of general and flexible approaches to asymmetric phosphines is often reflected in their price, which can rival the cost of precious metal portion of the catalyst. Accordingly, there is a need for new, efficient, and enantioselective methods for the preparation of chiral phosphines and related compounds, and well as methods for the preparation of intermediates for the preparation of such compounds.

SUMMARY

Disclosed herein are methods for the preparation of novel classes of chiral phosphine ligands via enantioselective copper-catalyzed halogenation in a rapid and flexible fashion. The approach also provides new methods for preparing useful intermediates for the preparation of chiral phosphines and other valuable compounds.

Thus disclosed herein are methods for the copper-catalyzed enantioselective transfer of halogens via 1,3-halogen migration. The Cu(I)-catalyzed 1,3-halogen migration reactions described herein effectively recycle an activating group by transferring the halogen from an $sp^2$ to a benzylic carbon with good enantioselectivity and concomitant borylation of the Ar-halogen bond. The resulting enantio-enriched benzyl halide can be reacted in the same vessel under a variety of conditions to form an additional carbon-heteroatom or carbon-carbon bond while maintaining high enantiomeric excess (ee). Migrations of aryl chlorides, bromides, and iodides can be accomplished. Experiments investigating non-linear effects indicate that the active catalyst species is monomeric in nature.

Also disclosed herein is a method to functionalize an arene comprising contacting an optionally substituted o-halostyrene with a hydroborane in the presence of an effective amount of copper(I), a base, and an electron-rich bidentate phosphine ligand, resulting in a 1,3-halogen migration of the o-halo group to the benzyl position resulting in hydrobromination and hydroboration at the position previously held by the o-halo group, to provide a compound that is both a benzyl halide and an aryl boronic ester.

Thus, one embodiment disclosed herein is a method to induce a 1,3-halogen a migration comprising contacting a compound of Formula (I):

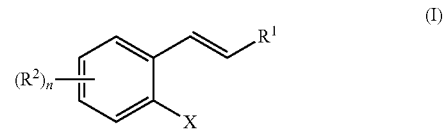

wherein
  X is Cl, Br, or I;
  $R^1$ is H, alkyl, aryl, heteroaryl, or cycloalkyl;
  $R^2$ is H, halo, alkyl, alkoxy, aryl, or heteroaryl; and
  n is 0, 1, 2, 3, or 4;
with a hydroborane in the presence of an effective amount of copper(I), a base, and an electron-rich bidentate phosphine ligand, to provide a compound of Formula (II):

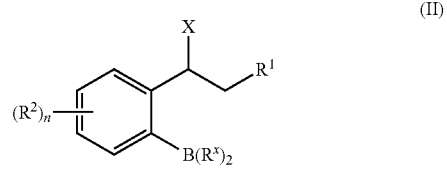

wherein each $R^x$ is independently a boron ligand or both $R^x$ groups together form a bidentate boron ligand.

Another embodiment is a method to enantioselectively induce a 1,3-halogen a migration comprising contacting a compound of Formula (I):

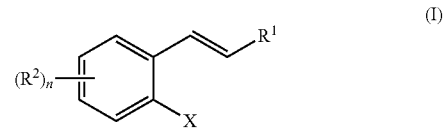

wherein
  X is Cl, Br, or I;
  $R^1$ is H, alkyl, aryl, heteroaryl, or cycloalkyl;
  $R^2$ is H, halo, alkyl, alkoxy, aryl, or heteroaryl; and
  n is 0, 1, 2, 3, or 4;
with a hydroborane in the presence of an effective amount of copper(I), a base, and a chiral electron-rich bidentate phosphine ligand, to provide an enantioenriched compound of Formula (II):

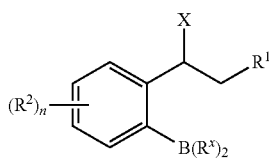
(II)

wherein each $R^x$ is independently a boron ligand or both $R^x$ groups together form a bidentate boron ligand. The resulting benzylic halides can then be displaced with a heteroatom nucleophile or a carbon nucleophile, and/or the compound can be coupled at the borate substituent to provide other useful compounds.

Also disclosed herein is a method for preparing a chiral ligand comprising contacting a compound of Formula (I):

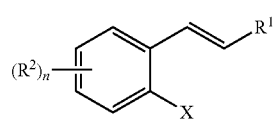
(I)

wherein
  X is Cl, Br, or I;
  $R^1$ is H, alkyl, aryl, heteroaryl, or cycloalkyl;
  $R^2$ is H, halo, alkyl, alkoxy, aryl, or heteroaryl; and
  n is 0, 1, 2, 3, or 4;
with a hydroborane in the presence of an effective amount of copper(I), a base, and an electron-rich bidentate phosphine ligand, to provide a compound of Formula (II):

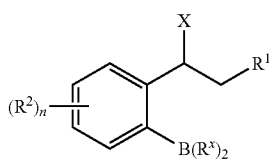
(II)

wherein each $R^x$ is independently a boron ligand or both $R^x$ groups together form a bidentate boron ligand; contacting the compound of Formula (II) with an excess of ammonia or an ammonia equivalent; and converting the boronate to a diphenylphosphine moiety to provide a chiral ligand of Formula (II-A):

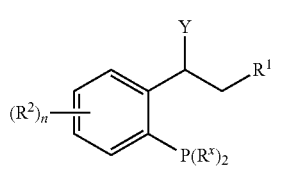
(II-A)

wherein Y is amino and $R^x$ is phenyl.

Further disclosed herein is a method for preparing a chiral ligand comprising contacting a compound of Formula (III):

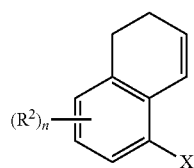
(III)

wherein
  X is Cl, Br, or I;
  $R^2$ is H, halo, alkyl, alkoxy, aryl, or heteroaryl; and
  n is 0, 1, 2, or 3;
with a hydroborane in the presence of an effective amount of copper(I), a base, and an electron-rich bidentate phosphine ligand, to provide a compound of Formula (IV):

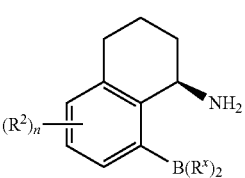
(IV)

wherein each $R^x$ is independently a boron ligand or both $R^x$ groups together form a bidentate boron ligand; contacting the compound of Formula (IV) with an excess of ammonia or an ammonia equivalent; and converting the boronate to a diphenylphosphine moiety.

In yet another embodiment, the disclosure includes a method for preparing a chiral ligand comprising contacting a compound of Formula (V):

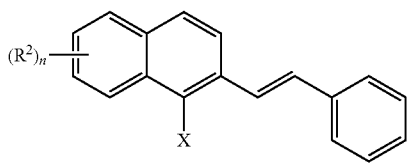
(V)

wherein
  X is Cl, Br, or I;
  $R^2$ is H, halo, alkyl, alkoxy, aryl, or heteroaryl; and
  n is 0, 1, 2, or 3;
with a hydroborane in the presence of an effective amount of copper(I), a base, and an electron-rich bidentate phosphine ligand, to provide a compound of Formula (VI):

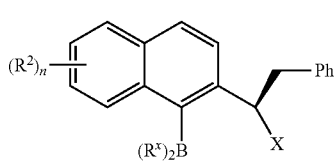
(VI)

wherein each $R^x$ is independently a boron ligand or both $R^x$ groups together form a bidentate boron ligand; contacting the compound of Formula (VI) with a compound of Formula (VIa):

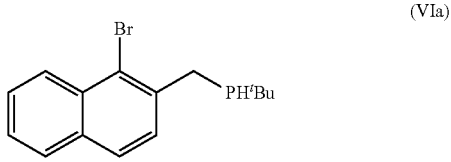

(VIa)

in the presence of an alkyl lithium agent to form a coupled product, oxidizing the coupled product to provide a phosphine, oxidizing the phosphine compound, to provide a phosphine oxide compound, cyclizing the phosphine oxide compound at the bromide and boronate moieties, dimerizing the resulting product in the presence of a strong base, and reducing the phosphine oxide moieties to phosphines, to provide a binapine chiral ligand.

Additional embodiments include a method for preparing a chiral ligand, the method comprising contacting a compound of Formula (I):

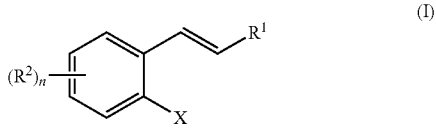

(I)

wherein
X is Cl, Br, or I;
$R^1$ is H, alkyl, aryl, heteroaryl, or cycloalkyl;
$R^2$ is H, halo, alkyl, alkoxy, aryl, or heteroaryl; and
n is 0, 1, 2, or 3;
with a hydroborane in the presence of an effective amount of copper(I), a base, and an electron-rich bidentate phosphine ligand, to provide a compound of Formula (II):

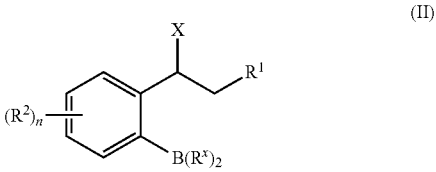

(II)

wherein each $R^x$ is independently a boron ligand or both $R^x$ groups together form a bidentate boron ligand; contacting the compound of Formula (II) with an excess of tert-butylphosphine oxide in the presence of a strong base to displace the benzylic halide with the tert-butylphosphine oxide, carrying out a hydroformylation reaction in the presence of a rhodium catalyst followed by cyclization, forming a dimer of the resulting product, and reducing the phosphine oxide moieties to provide a DuanPhos derivative chiral ligand of Formula (VII):

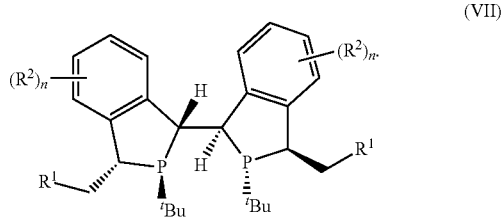

(VII)

Another embodiment disclosed herein provides a process to prepare a catalyst composition, comprising contacting a transition metal such as palladium and a phosphine ligand corresponding to any formula described herein, under conditions such that a catalyst composition is formed.

Also disclosed herein are novel compounds of the formulas described herein, intermediates for the synthesis of the formulas described herein, as well as methods of preparing of the formulas described herein. The compounds described herein are useful as intermediates for the synthesis of other useful compounds, such as therapeutic agents and ligands for catalysis.

DETAILED DESCRIPTION

This disclosure describes the Cu-catalyzed 1,3-migration of a halogen from an aryl to a benzylic position with concomitant borylation of the aryl halide. Additionally, this transformation has now been rendered enantioselective using an asymmetric bidentate phosphine ligand to give scaffolds in high enantiomeric excess (ee). Clean inversion of the stereochemistry at the benzylic carbon has been accomplished with heteroatom and carbon nucleophiles, including alcohols, amines, anilines, azides, thiols, malonates, enolates and phosphines. This new chemistry can be applied to both streamlining the preparation of known phosphines and synthesizing novel classes of ligands with applications in a wide range of important enantioselective transformations. New ligands containing point chirality at carbon and phosphorus, as well as combinations of axial and point chirality, can be prepared. This new methodology also allows for the flexible formation of PBP, PPP and PNP pincer ligands and novel trans-spanning ligands. These ligands can be employed with an array of transition metals to accomplish enantioselective synthetic transformations that include, but are not limited to, cross-coupling, reductions, carbon-carbon bond-forming reactions and small molecule incorporation.

The synthesis of enantioenriched phosphine ligands often requires multiple synthetic manipulations and resolution steps. The difficulty in preparing valuable asymmetric phosphines can result in a very high cost associated with the ligand that often rivals the cost of the metal catalysts employed in a range of important organic transformations. This disclosure provides the ability to prepare both known and novel new phosphine ligands in a more economical and flexible process than current approaches. Additionally, new ligands prepared by the methods can exhibit improved reactivity and enantioselectivity compared to commercially available compounds.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the disclosure encompasses not only the entire group listed as a whole, but each member of the group individually and all possible subgroups of the main group. Additionally, for all purposes, the disclosure encompasses not only the main group, but also the main group absent one or more of the group members. The disclosure therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

Specific values listed below for radicals, substituents, and ranges, are for illustration only; they do not exclude other defined values or other values within defined ranges for the radicals and substituents. However, certain values or ranges of values can optionally be excluded from certain embodiments in the form of negative limitations.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent as described for Formula (I) or Formula (II), or a substituent as described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

Substituted alkyl groups may include haloalkyl groups. The term "haloalkyl" refers to alkyl as defined herein substituted by 1-20 halo groups, typically 1-5 halo groups, which may be the same or different. Representative haloalkyl groups include, by way of example, trifluoromethyl, tetrafluoroethyl ($-CF_2CF_3$), 3-fluorododecyl, 12,12,12-trifluorododecyl, 2-bromooctyl, 3-bromo-6-chloroheptyl, perfluorooctyl, and the like.

The term "alkoxy" refers to the group —O-alkyl, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent (e.g., linking two groups together), and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine.

By way of example and not limitation, carbon bonded heterocycles can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like. Various combinations of the aforementioned positions are included in the compounds described herein.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, tetramethylene, or 1,2-methylenedixoy diradical thereto.

The term "halo" refers to fluoro, chloro, bromo, or iodo. In some embodiments, halo can refer to only chloro, bromo, and iodo, as appropriate.

"Amino" refers to $-NH_2$. Amino groups can be substituted, for example with an alkyl group to form an "alkylamino", e.g., $-NR_2$, wherein at least one R is alkyl and the second R is alkyl or hydrogen. The term "acylamino" refers to RC(=O)NH—, wherein R is alkyl or aryl. The alkyl group can be, for example, a $C_1-C_6$ alkyl group. Examples include, but are not limited to methylamino and ethylamino. The group may be a terminal group or a bridging group, and the alkyl groups may be substituted.

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Additionally, suitable substituent groups can be, e.g., —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, —NC(=O)R, —C(=O)R, —C(=O)NRR, —S(=O)₂O⁻, —S(=O)₂OH, —S(=O)₂R, —OS(=O)₂OR, —S(=O)₂NR, —S(=O)R, —OP(=O) (OR)₂, —P(=O)(OR)₂, —OP(=O)(OH)(OR), —P(=O) (OH)(OR), —P(=O)(O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with one or more of the substituents above.

Alkyl chains can be optionally interrupted, for example, with one or more heteroatoms. The term "interrupted" indicates that another group is inserted between two adjacent carbon atoms, and the hydrogen atoms to which they are attached (e.g., methyl ($CH_3$), methylene ($CH_2$) or methine (CH)), of a particular carbon chain being referred to in the expression using the term "interrupted", provided that each of the indicated atom's normal valency is not exceeded, and that the interruption results in a stable compound. Suitable groups that can interrupt a carbon chain include, e.g., with one or more non-peroxide oxy (—O—), thio (—S—), imino (—N(H)—), methylenedioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl ($SO_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached. An alkyl group that is interrupted by a heteroatom therefor forms a heteroalkyl group.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "enantiomerically enriched" refers to mixtures that have one enantiomer present to a greater extent than another. In one embodiment, the term "enantiomerically enriched" refers to a mixture having at least about 50% enantiomeric excess ("ee"). In other embodiments, the enantiomerically enriched products described herein can have at least about 75% ee, at least about 80% ee, at least about 85% ee, at least about 90% ee, at least about 92% ee, at least about 95% ee, at least about 97% ee, at least about 98% ee, or at least about 99% ee.

Hydrohalogenation of Olefins and Application of Enantioselective Copper-Catalyzed Halogenation to the Synthesis of Novel Chiral Ligands:

Chiral, non-racemic phosphines are crucial components in a multitude of important enantioselective transformations. However, their syntheses can require multiple steps and difficult chiral resolution. General and flexible approaches to asymmetric phosphines are therefore needed in the art.

We have described the Cu-catalyzed 1,3-migration of a halogen in 1.1 from an aryl to a benzylic position with concomitant borylation of the aryl halide (Grigg et al., *J. Am. Chem. Soc.* 2012, 134, 16131; Grigg et al., *Synlett*, 2013, 24, 401). The transformation has recently been rendered enantioselective using an asymmetric bidentate phosphine ligand to give scaffolds like 1.2 in high ee (Scheme 1). Clean inversion of the stereochemistry at the benzylic carbon has been accomplished with heteroatom and carbon nucleophiles, including alcohols, amines, anilines, azides, thiols, malonates, enolates and phosphines.

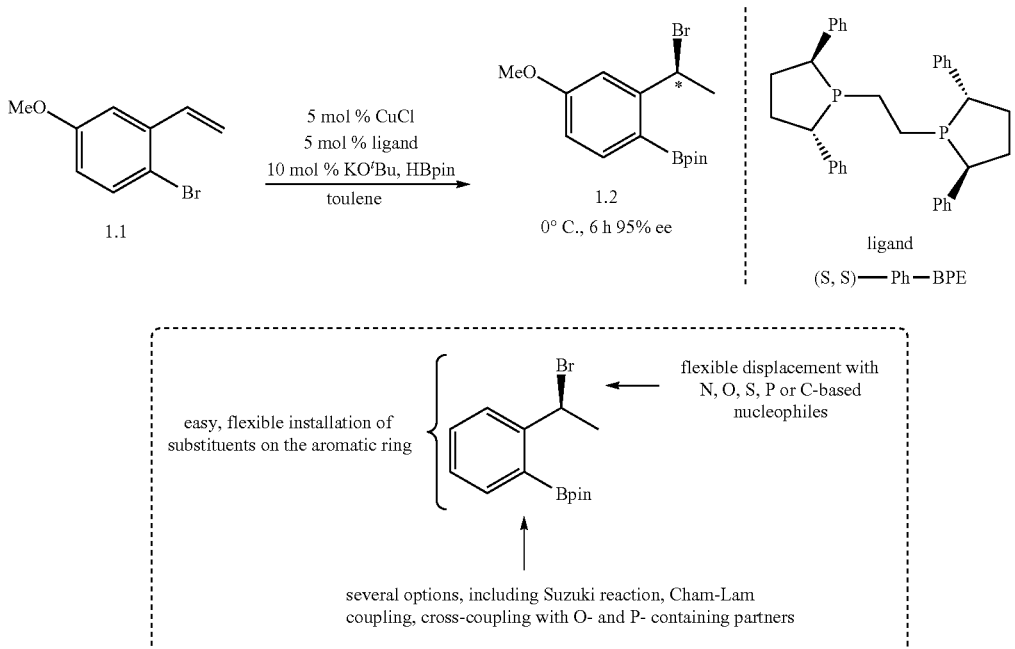

Scheme 1.2 Enantioselective Cu-catalyzed halogenation.

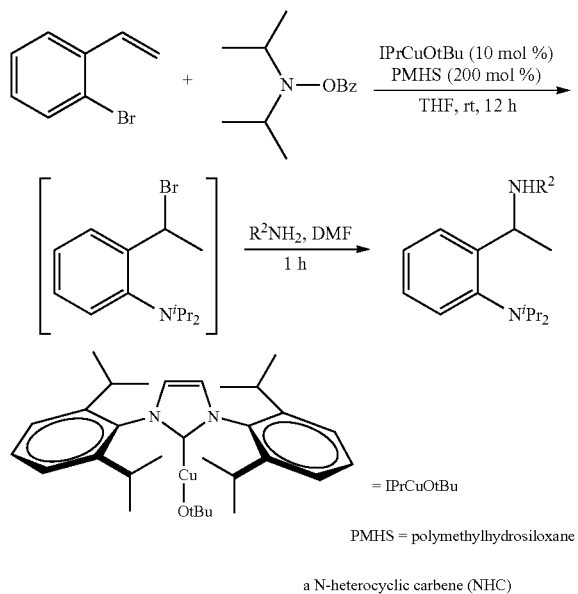

The methods can be used for the rapid and flexible preparation of known phosphines and novel classes of ligands, including diamine ligands, with applications in a range of important enantioselective transformations. Reaction substrates can include either commercially available or easily synthesized materials and the methods are highly modular and tunable.

New ligands that can be prepared include ligands containing point chirality at both carbon and phosphorus, axial and point chirality, PBP/PPP/PNP pincer ligands and novel trans-spanning ligands. The ligands can be used in a variety of reactions including cross-coupling, reductions, carbon-carbon bond-formation and small molecule incorporation (carbonylation, hydroformylation and carboxylation reactions).

New Mono- and Bidentate Phosphine Ligands Chiral at Carbon.

Libraries of C1 and C2 symmetric ligands can be accessed through a straight-forward sequence involving nucleophilic displacement of the benzyl bromide with a primary or secondary phosphine (Scheme 2). Dialkylation of a primary phosphine with the benzyl halide 2.2 leads to ligands of the form 2.3. Alternatively, if the key intermediate 2.2 is treated with a secondary, achiral phosphine, the result is a monodentate phosphine 2.5. Hydrolysis of the boronic esters of both 2.3 and 2.5 can yield boronic acids that can undergo reversible reaction with substrates containing alcohols and amines. This "scaffolding approach" can impart excellent regio- and stereocontrol to alkene functionalizations.

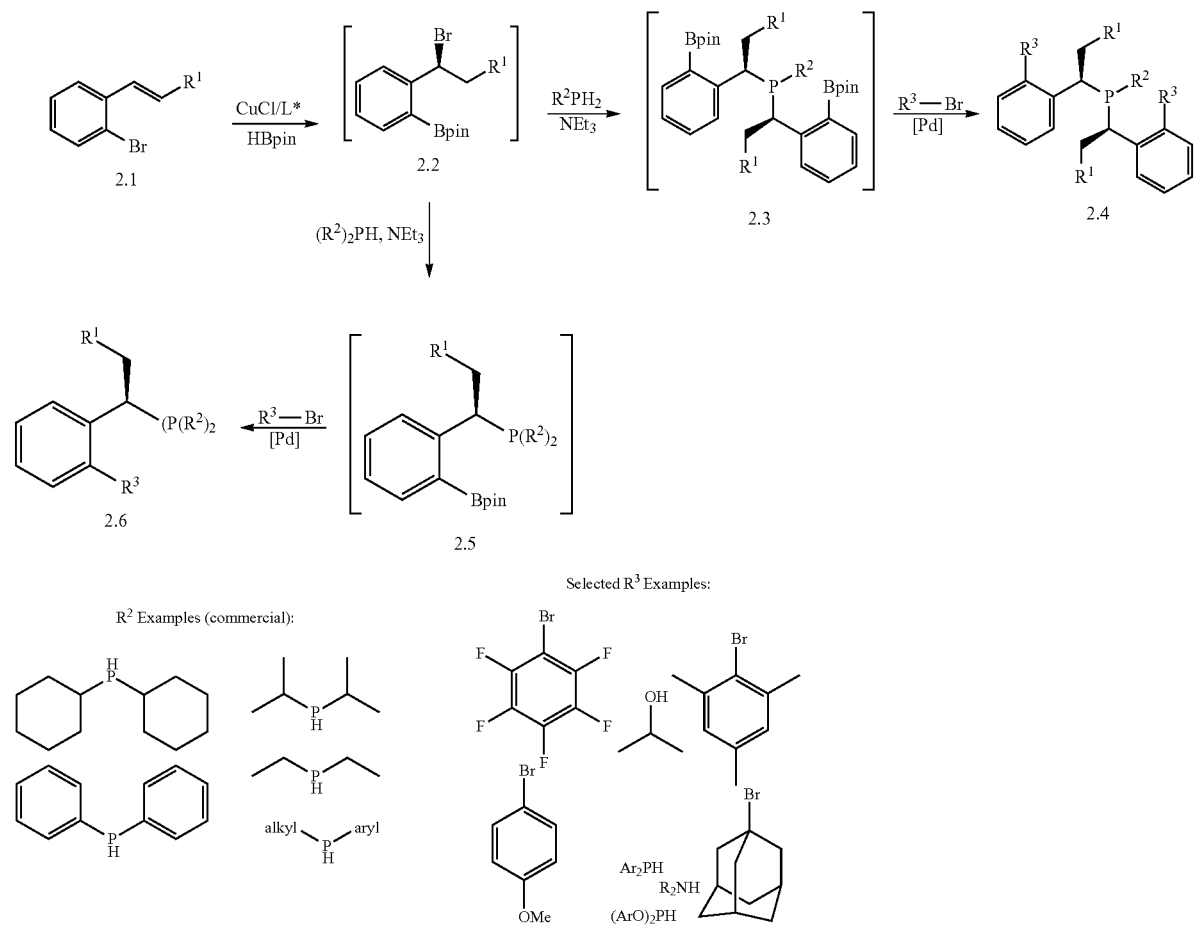

Scheme 2. C1- and C-2 symmetric ligands with point chirality at carbon.

C2 symmetric ligands of the form 2.4 can be accessed by simple transformation of the boronic ester via Suzuki coupling, Chan-Lam coupling or oxidation. Suzuki coupling of the remaining boronic ester of 2.5 with a variety of aryl or alkyl halides can provide monodentate C1 symmetric ligands of the form 2.6. These ligands mimic Buchwald-type ligands in terms of their steric and electronic properties, but have a chiral center that can be used for enantio- or diastereoselective transformations. To provide additional new classes of bidentate ligands, the C—B bond of 2.5 can be transformed into a C—N or C—P bond (2.6, $R^3$=$NR_2$, $PR_2$, where each R can independently be an optionally substituted alkyl, aryl, cycloalkyl, heterocycle, heteroaryl, dialkylamine, diarylphosphine, or diaryloxyphosphine).

Ligands with Adjacent Point Chirality at the Carbon and Phosphorus Centers.

Ligands containing chirality at adjacent carbon and phosphorus atoms are uncommon, but can exhibit superior performance compared to ligands with chirality only at carbon or phosphorus. The new enantioselective halogenation described herein permits facile access to these types of motifs using two different approaches (Scheme 3). A chiral phosphine can be employed as the nucleophile to transform 3.1 to 3.3, and eventually to 3.4a (where $R^4$ can be as defined for $R^3$, and $R^2$ and $R^3$ can be defined as R in Scheme 2 above). Alternatively, two successive alkylations of 3.2 can be carried out with two different phosphines to yield 3.6a and/or 3.6b. When the chirality at the benzylic carbon controls the stereochemical outcome at the phosphorus center, this approach provides a very modular and inexpensive way to access phosphine ligands containing point chirality at adjacent carbon and phosphorus centers.

Ligands with Axial Chirality and Point Chirality at Phosphorus.

Enantioselective halogenation can be applied to the synthesis of an intriguing new class of ligands starting from ortho-bromostyrenes 4.1 containing a suitably bulky substituent at $R^2$ (where $R^2$=alkyl, alkoxy, cycloalkyl, cycloalkoxy, etc. (e.g., as defined for other R groups herein)). Cu-catalyzed asymmetric 1,3-halogen migration, nucleophilic displacement and Suzuki coupling of an intermediate similar to 2.5 (see Scheme 2) with an ortho-substituted aryl halide leads to a biaryl 4.2 that contains axial chirality. The chiral benzylic carbon center can assist in controlling the production of a single atropisomer. Any mixtures of atropisomers can be separated to yield diastereomeric ligands with both point and axial chirality in close proximity.

Scheme 4. New ligand classes with point and axial chirality.

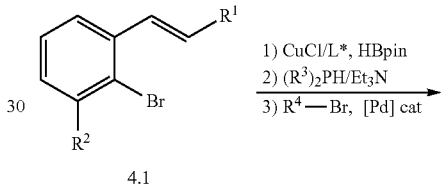

4.1

$R^2$ = Me, OMe, etc.

Scheme 3. C1 and C2 symmetric ligands with point chirality at both carbon and phosphorus.

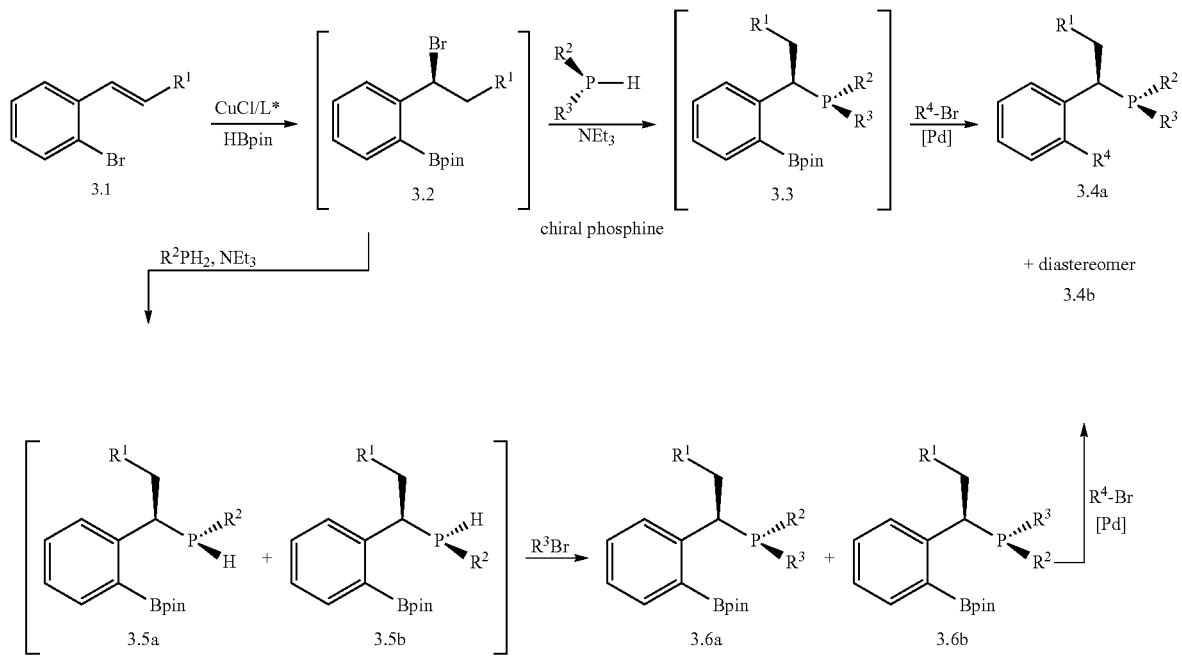

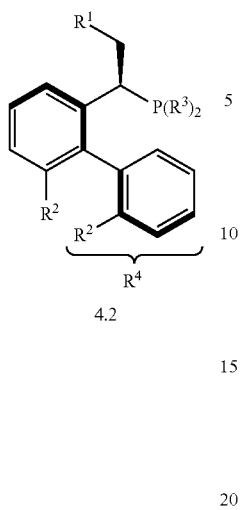
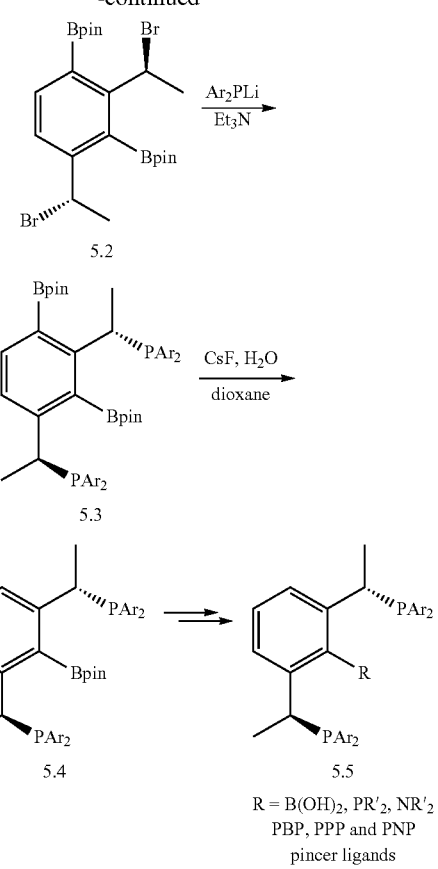

Phosphorus-Containing Pincer Ligands.

Pincer ligands are chelating ligands that are capable of binding to three adjacent coplanar sites on a transition metal. The tight binding imparts high thermal stability to the resulting complexes and prevents competing cyclometallation. The preparation of new classes of C2 symmetric pincer ligands (Scheme 5) can be prepared by employing a dual Cu-catalyzed 1,3-halogen migration on 5.1 to yield 5.2, where the less hindered alkene of 5.1 reacts first. Double displacement of the resulting benzyl bromides with a phosphorus nucleophile can provide aryl 5.3. Protodeboronation of the more sterically accessible aryl boronic acid can provide the C2 symmetric PBP pincer-type ligand 5.4. The remaining boronic ester can then be reacted with suitable phosphorus and nitrogen-containing coupling partners to access PPP and PNP ligands of the form 5.5. Protodeborylation of both of the boronic esters of 5.3 can yield a PCP ligand. Alternatively, the halogens of 5.2 can be displaced with phosphorus oxides, followed protodeboronation and by coupling the resulting compound with a desired R group (e.g., B(OH)$_2$, PR$_2$, or NR$_2$), and final reduction of the phosphorus oxide moieties to phosphines, to provide the ligands 5.5. As with other schemes of this disclosure, the bromide shown in Scheme 5 can be chloride or iodide, Bpin can be other boron moieties as described herein, Ar can be an aryl group, optionally substituted, as described in the definition for aryl groups herein, and R' can be any relevant substituent as described herein, for example, a suitable substituent for phosphorus or nitrogen such as alkyl, aryl, cycloalkyl, heteroaryl, heterocycle, and the like, each optionally substituted.

Scheme 5. Novel phosphorus-containing pincer ligands.

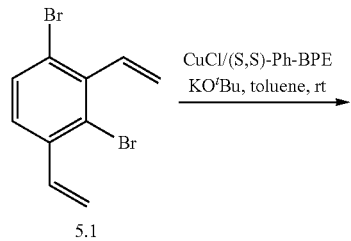

Trans-Spanning Bidentate Ligands.

Trans-spanning ligands occupy opposite sites of transition metal complexes that have square-planar coordination geometries. These ligands often exhibit very different modes of catalysis compared to ligands that chelate to metals in a cis fashion. Scheme 6 illustrates two different trans-spanning ligands, 6.2 and 6.3, that are accessible using enantioselective 1,3-halogen migration.

Scheme 6. Trans-spanning ligands.

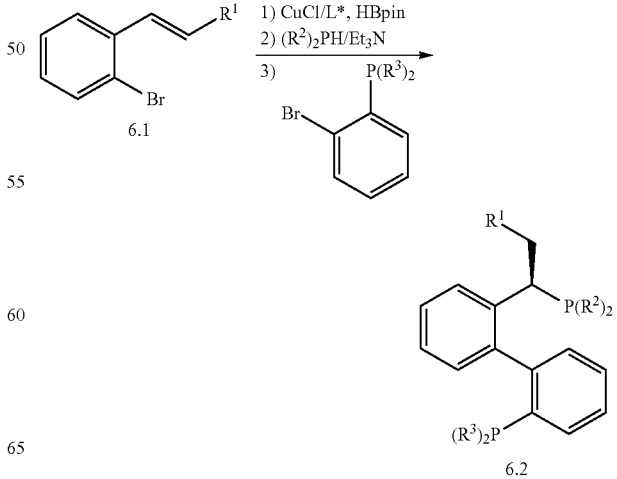

19

-continued

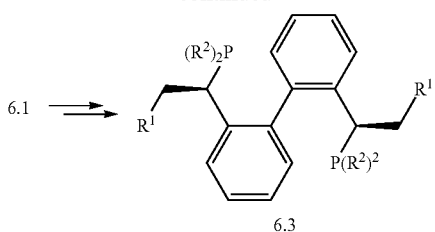

6.1 ⟶

6.3

Test Reactions for Exploring the Efficacy of New Ligand Sets.

The catalytic and enantioselective abilities of new ligands can be evaluated using a standard set of transformations that have been accomplished with varying degrees of success using other asymmetric phosphine ligands (Scheme 7). These reactions include cross-coupling, reductions of both C=C and C=O bonds, reactions involving the incorporation of small gaseous molecules like CO, cyclizations and enantioselective additions to imine, conjugate additions and $S_N2'$ reactions.

Scheme 7. Test reactions for novel ligands.

Cross-coupling

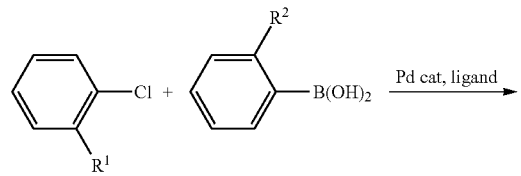

axial chirality

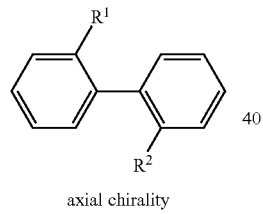

20

-continued

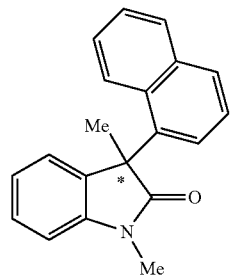

Asymmetric reduction

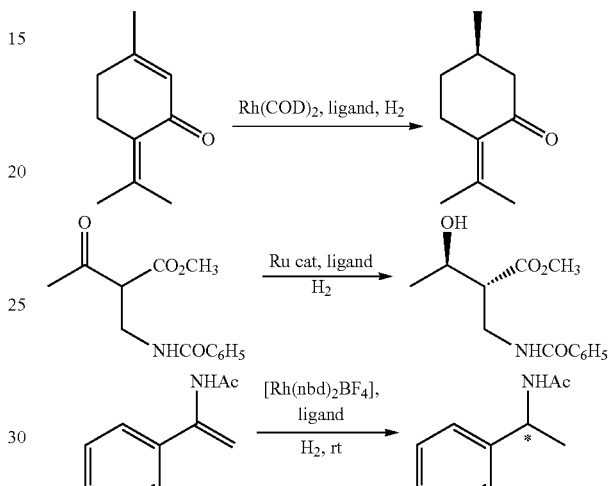

Small molecule incorporation

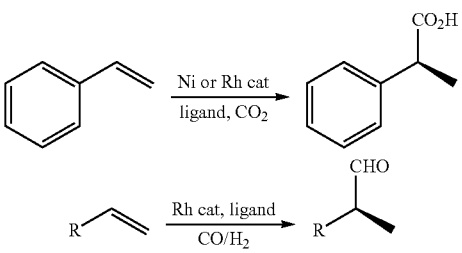

Cyclizations

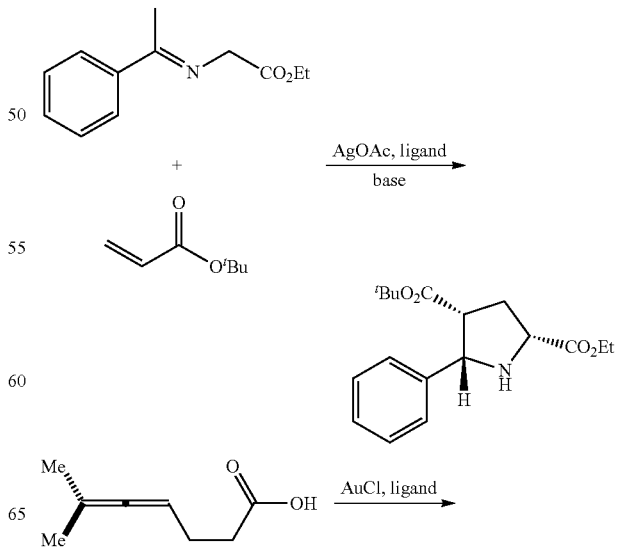

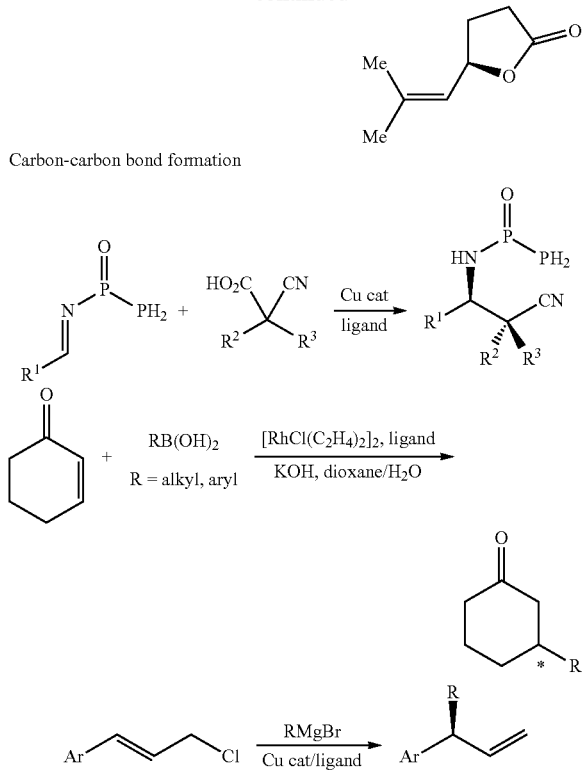

Carbon-carbon bond formation

General Synthetic Methods:

Disclosed herein are methods of making various benzylic halides, such as compounds of Formula (II). The compounds can be prepared either racemically or in enantioenriched form. Also disclosed herein are novel syntheses of various ligands, including the phosphine ligands of Formulas (II-A), (IV), (VI), (VII), as described herein. Certain individual synthetic transformations for their preparation and modification are well known in the art. Many of these known techniques are elaborated in the *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as *March's Advanced Organic Chemistry: Reactions, Mechanisms, and Structure, $5^{th}$* Ed., by M. B. Smith and J. March (John Wiley & Sons, New York, 2001); *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., $2^{nd}$ Ed., John Wiley & Sons, New York (1999).

A number of exemplary methods for the preparation of the compositions are provided herein. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be -100° C. to 200° C., as necessary for the reaction of interest, solvents will be aprotic or protic depending on the conditions required, and reaction times can be about 1 minute to about 2 days. Work-up typically consists of quenching any unreacted reagents followed by partition between a water/organic layer system (extraction) and separation of the layer containing the product of interest.

Oxidation and reduction reactions are typically carried out at temperatures near room temperature (about 23° C.), although for metal hydride reductions frequently the temperature is reduced to 0° C. to -100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to -100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and can be applied when applicable.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group or heteroatom. The particular removable blocking group employed is not always critical and preferred removable hydroxyl blocking groups include conventional groups such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product. The R groups of various schemes and formulas herein can also be protecting groups, such as the protecting groups described above and in various literature cited herein.

Suitable protecting groups are known to those skilled in the art and disclosed in more detail by T. W. Greene, *Protecting Groups In Organic Synthesis*; Wiley: New York, 1981 ("Greene") and the references cited therein, and by Kocienski, Philip J.; *Protecting Groups* (Georg Thieme Verlag Stuttgart, N.Y., 1994), both of which are incorporated herein by reference.

Protecting groups are available, commonly known and used, and are optionally used to prevent side reactions with the protected group during synthetic procedures, i.e. routes or methods to prepare various compounds by the methods described herein. For the most part the decision as to which groups to protect, when to install and remove the protecting groups, and the nature of the chemical protecting group "PG" will be dependent upon the chemistry of the reaction to be protected against (e.g., acidic, basic, oxidative, reductive or other conditions) and the intended product of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups can be dependent upon the intended products of the synthesis and the reaction conditions to be encountered, and may occur in any order as determined by the artisan.

Various functional groups of the compounds disclosed herein may be protected. For example, protecting groups for —OH groups (whether hydroxyl, carboxylic acid, or other functions) include "ether- or ester-forming groups". Many ether- or ester-forming groups are capable of functioning as chemical protecting groups in the synthetic schemes set forth herein. However, some hydroxyl and thio protecting groups are neither ether-nor ester-forming groups, as will be understood by those skilled in the art. For further detail regarding carboxylic acid protecting groups and other protecting groups for acids, see Greene, cited above. Such groups include by way of example and not limitation, amides, hydrazides, and the like.

As to any of the compounds and formulas described herein, which contain one or more substituents, it is understood, of course, that such groups do not contain any substitution or substitution patterns that are sterically impractical and/or synthetically non-feasible. It will be appreciated that the compounds on may contain asymmetrically substituted carbon atoms and thus may be prepared and isolated in either optically active or racemic forms. All chiral, diastereomeric, and racemic forms and all geometric isomeric forms of the compounds described herein, individually and/or collectively, are encompassed by the present disclosure.

One diastereomer may display superior activity compared to another. When required, separation of racemic materials can be achieved by high performance liquid chromatography (HPLC) using a chiral column or by a resolution using a resolving agent such as camphonic chloride, as in Thomas J. Tucker et al., *J. Med. Chem.* 1994, 37, 2437-2444. A chiral compound may also be directly synthesized using a chiral catalyst or a chiral ligand (see, for example, Mark A. Huffman, et al., *J. Org. Chem.* 1995, 60, 1590-1594) or by the techniques described herein.

In general, modifications to the compounds and formulas described herein can be made according to organic synthesis techniques known to those of skill in the art and/or according to the synthetic schemes provided herein. Where desired, synthesis of a subject compound can begin with commercially available chemicals, from compounds described in the chemical literature, or from products of the reactions and methods described herein. Commercially available compounds may be obtained from standard commercial sources including Acros Organics (Pittsburgh Pa.), Aldrich Chemical (Milwaukee Wis., including Sigma Chemical and Fluka), Eastman Organic Chemicals, Eastman Kodak Company (Rochester N.Y.), Fisher Scientific Co. (Pittsburgh Pa.), ICN Biomedicals, Inc. (Costa Mesa Calif.), Lancaster Synthesis (Windham N.H.), Spectrum Quality Product, Inc. (New Brunswick, N.J.), TCI America (Portland Oreg.), and Wako Chemicals USA, Inc. (Richmond Va.).

Compounds and Methods:

As described in the Summary, disclosed herein are methods for carrying out 1,3-halogen migrations. In one embodiment, the method includes a method to functionalize an arene comprising contacting an optionally substituted o-halostyrene with a hydroborane in the presence of an effective amount of copper(I), a base, and an electron-rich bidentate phosphine ligand, resulting in a 1,3-halogen migration of the o-halo group to the benzyl position resulting in hydrobromination and hydroboration at the position previously held by the o-halo group, to provide a compound that is both a benzyl halide and an aryl boronic ester.

In various embodiments, the benzylic halogen formed in the reaction can be displaced with a heteroatom nucleophile or a carbon nucleophile, as described herein.

In one embodiment, the compound of Formula (I) is:

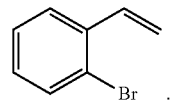

In another embodiment, the compound of Formula (I) is:

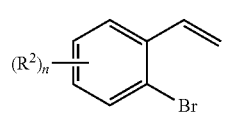

(I-A)

wherein n is 1, 2, 3, or 4.

In one embodiment, the product of the reaction is:

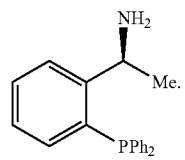

In one embodiment, the compound of Formula (III) is:

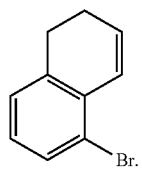 [SMILES: Brc1cccc2c1C=CCC2]

In one embodiment, the product of the reaction is:

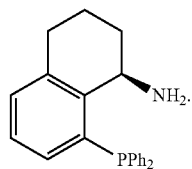

In one embodiment, the compound of Formula (V) is:

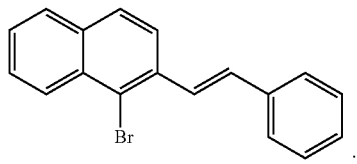 [SMILES: Brc1c(/C=C/c2ccccc2)ccc2ccccc12]

In one embodiment, the product of the reaction is:

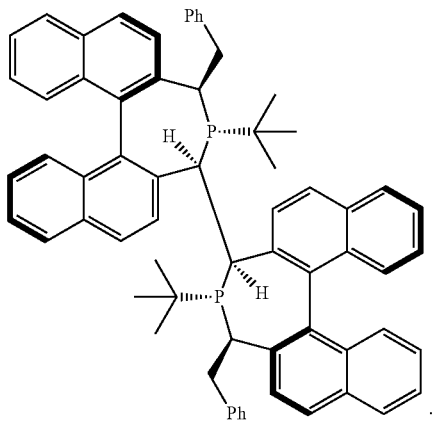

In other embodiments, the t-butyl groups on the phosphorus atoms are replaced by aryl groups or other alkyl groups, and/or the nathyl rings are substituted with R groups are described herein.

In one embodiment, the electron-rich bidentate phosphine ligand can be, for example, dCype. In another embodiment, such as for enantioselective reactions, the chiral electron-rich bidentate phosphine ligand is (S)-1-(2-(diphenylphosphino) phenyl)ethanamine ("(S,S)-Ph-BPE"). When (S,S)-Ph-BPE is used as a ligand, the product chiral ligand can be provided in an ee of greater than about 80%, greater than about 85%, greater than about 90%, or greater than about 95%.

Suitable reaction conditions can include the use of 0.1-20 mol %, or about 5-10 mol %, of a copper(I) catalyst, 0.1-20 mol %, or about 5-10 mol %, of an effective ligand, and 1-40 mol %, or about 10-20 mol %, of an effective base. In one embodiment, the copper(I) is formed from CuCl. The base can be, for example, an alkali metal alkoxide such as sodium or potassium t-butoxide. Other useful copper(I) catalysts can be provided by the use of reagents such as CuBr, CuI, CuOTf, CuOTs, and the like.

Common specific aryl substituents of the phosphine ligand described herein (e.g., various R groups such as R, $R^1$, $R^2$, $R^3$, $R^4$, or $R^5$) include H; linear, branched or cyclic $C_1$-$C_{20}$ alkyl, $C_6$-$C_{18}$ aryl, and $C_1$-$C_{20}$ alkoxy; $C_1$-$C_{20}$ dialkylamino; halogen; and trifluoromethyl. Additional examples of substituents on substituted groups (such as aryl groups, heteroaryl groups, and the like) can include but are not limited to any substituent that does not interfere with a particular desired reaction, such as alkyl (for example, $C_1$-$C_{12}$), alkenyl (for example, $C_2$-$C_{12}$), alkynyl (for example, $C_2$-$C_{12}$), alkoxy (for example, $C_1$-$C_{12}$), acyloxy (for example, $C_1$-$C_{12}$), aryloxy, aryl, heteroaryl, F, Cl, OH, $NO_2$, COOH, CHO, $SO_3H$, $SO_2$, SOR, $NH_2$, NH-alkyl (for example, $C_1$-$C_{12}$), N-dialkyl (for example, $C_1$-$C_{12}$), haloalkyl (e.g., trihalomethyl), NHCO-alkyl (for example, $C_1$-$C_8$), CONH-alkyl (for example, $C_1$-$C_4$), CON-dialkyl (for example, $C_1$-$C_4$), COO-alkyl (for example, $C_1$-$C_{12}$), $CONH_2$, CO-alkyl (for example, $C_1$-$C_{12}$), NHCOH, NHCOO-alkyl (for example, $C_1$-$C_8$), CO-aryl, COO-aryl, $CHCHCO_2$-alkyl (for example, $C_1$-$C_{12}$), $CHCHCO_2H$, PO-diaryl, and PO-dialkyl (for example, $C_1$-$C_8$). One of skill in the art will understand that the presence of a substituent having an active hydrogen atom (e.g., OH, $CO_2H$, CONH-alkyl and the like) may be protected with a suitable protecting group (PG). Additional useful methods for preparing asymmetric phosphine ligands and substituted asymmetric phosphine ligands are described by U.S. Pat. No. 6,624,320 (Matsumura et al.).

Borylation.

Many useful reactions for the preparation of compounds described herein include borylation. The term "borylate" or "borylation" refers to modifying a carbon-hydrogen bond (or other carbon-"leaving group" bond) to provide a carbon-boron bond. Useful reagents for borylation include pinacolborane (HBpin), bispinacolatodiboron ($B_2pin_2$), or equivalent boron containing compounds. The term "bis(pinacolato)diboron" ($B_2pin_2$) refers to the diborane compound having the structure

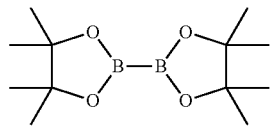

$B_2pin_2$ can be used to prepare useful compounds and complexes as described herein; however other diolate-substituted boranes can also be used in place of $B_2pin_2$ for preparing the catalysts and carrying out the methods described herein. Examples of other effective boranes for preparing compounds and catalysts and carrying out the methods described herein include derivatives of $B_2pin_2$ and dioxaborolanes such as pinacolborane (HBpin), 4-tert-butylcatechol-borane, 4-tert-butylcatecholborane (HBcat), hexyleneglycolato diborons, and various borane compounds. Examples of such useful boron reagents are further described in U.S. Pat. No. 6,451,937 (Hartwig et al.). Methods for preparing and using boronic acids and boronate esters are further described by U.S. Patent Publication No. 2006/0205966 (Westcott et al.) and references cited therein.

Solvent Systems.

The reactions described herein are typically carried out in the presence of a solvent or solvent system (a combination of two or more solvents), and use can be made of a usual solvent which does not adversely influence the reaction. Typical solvents include inert solvents including ethers such as diethyl ether, diisopropyl ether, tetrahydrofuran (THF), 1,4-dioxane, or 1,2-dimethoxyethane, hydrocarbons such as pentane, hexane, or methylcyclohexane, aromatic hydrocarbons such as benzene, toluene, or chlorobenzene, halogenated hydrocarbons such as chloroform, dichloromethane, 1,2-dichloroethane, or carbon tetrachloride; or other useful solvents such as acetonitrile. These solvents may be used solely or as a mixed solvent system. Furthermore, reactions can be suitably carried out under an inert gas atmosphere such as argon or nitrogen.

Ligands for the Copper-Catalyzed 1,3-Halogen Migration Reactions.

A variety of phosphine ligands can be used to facilitate the copper-catalyzed 1,3-halogen migration reactions. Suitable and effective ligands must prevent immediate borylation of the benzyl Cu—C bond. Racemic reactions are suitably facilitated by bulky, electron-rich bidentate phosphine ligands such as dCype [1,2-bis(dicyclohexylphosphino)

ethane], (1S,1S',2R,2R')-TangPhos, and dppbz [1,2-bis(diphenylphosphino)benzene]. The reaction can be rendered enantioselective with asymmetric electron-rich, bulky, bidentate phosphine ligands. Suitable and effective examples can include chiral ligands such as DIPAMP, o-tolyl-DIPAMP, 1-naphthyl-DIPAMP, iPr-DuPhos, iPr-BPE, and DuanPhos, and excellent enantioselectivity can be achieved with the use of (S,S)-Ph-BPE. Lowering the reaction temperature (e.g., to 25° C. or 0° C.) can increase the enantioselectivity. Reversed stereoselectivity can be achieved with the corresponding enantiomeric ligands.

Catalyst Compositions.

Disclosed is a process to prepare a catalyst composition, the process comprising contacting a transition metal or metal salt and a phosphine ligand corresponding to any a formula described herein, under conditions such that a catalyst composition is formed. The transition metal catalyst can be formed from transition metal salts and complexes of transition metal salts such as $PdCl_2$, $PdBr_2$, $PdI_2$, $Na_2PdCl_4$, $PdCl_2(PPh_3)_2$, $Pd(PPh_4)_3$, $RhCl(PPh_3)_3$, $Rh(acac)(P2)$, wherein acac is acetylacetonato and P2 represents two monodentate phosphine ligands or one bidentate phosphine ligand described herein, $Rh(acac)(L2)$, wherein acac is acetylacetonato and L represents a bidentate or two monodentate Lewis basic ligands. The Lewis basic ligands may be selected from, for example, imines, amines, pyridines and carbenes.

EXAMPLES

The following Examples are intended to illustrate the method disclosed herein and should not be construed to narrow its scope. One skilled in the art will readily recognize that the Examples suggest many other ways in which the method could be practiced. It should be understood that numerous variations and modifications may be made while remaining within the scope of the attached claims.

Example 1

Cu-Catalyzed Recycling of Halogen Activating Groups via 1,3-Halogen Migration A Cu(I)-catalyzed 1,3-halogen migration reaction effectively recycles an activating group by transferring bromine or iodine from an $sp^2$ carbon to a benzylic carbon with concomitant borylation of the Ar—X bond. The resulting benzyl halide can be reacted in the same vessel under a variety of conditions to form an additional carbon-heteroatom bond. Cross-over experiments using an isotopically enriched bromide source indicate intramolecular transfer of Br. The reaction proceeds via a Markovnikov hydrocupration of the o-halostyrene, oxidative addition of the resulting Cu(I) complex into the Ar—X bond, migration of the copper to the halogen-bearing carbon with accompanying dearomatization, then migration of the halogen to the benzylic carbon to re-establish aromaticity and generate an aryl copper(I) species, followed by a final borylation of an Ar—Cu(I) species to turn over the catalytic cycle.

Typically, aryl halides or pseudohalides are employed to provide reliable regioselectivity. However, use of an activating group imbues these transformations with less-than-ideal atom economy, as only one new bond is formed at the expense of the waste product. Direct C—H functionalization eliminates the need for preactivation, yet the need for additives in many of these reactions means it is not a foregone conclusion that this approach is less wasteful. Important advances have recently been made toward more practical and general directing groups for C—H functionalization, but the use of halide or pseudohalide activating groups remains the most convenient and commonly employed route to aryl functionalization. We felt that the use of activating groups might be more attractive if a way to "recycle" the halide could be developed. In this Example, we describe a Cu-catalyzed 1,3-halogen migration/borylation reaction that permits a halogen activating group to be used for the sequential formation of two new carbon-heteroatom bonds (Scheme 1-1).

Scheme 1-1. New Mode of Arene Functionalization.

Typical approach:

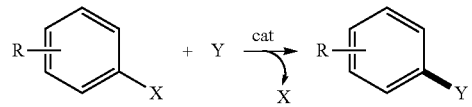

This work via recycling the activating group:

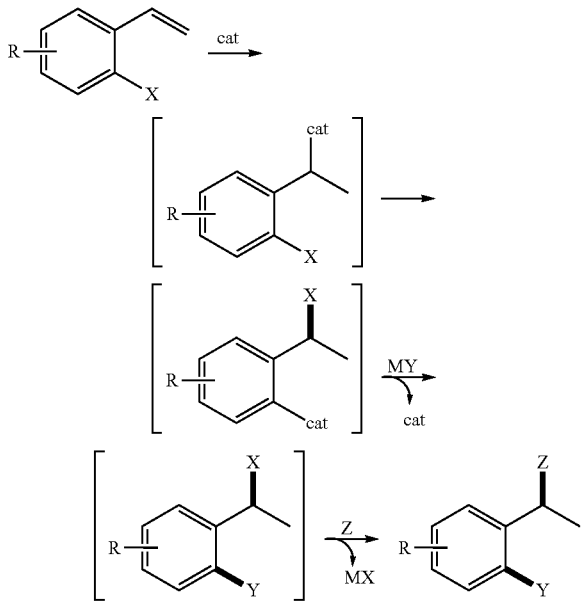

Conventional arene functionalization utilizes a range of transition metal catalysts and coupling partners to transform aryl-X bonds into new carbon-carbon or carbon-heteroatom bonds. Conceptually, the current approach differs in that the catalyst does not interact with the C—X bond directly, but rather with a functional group, such as an olefin. "M" in "MX" is a transition metal, such as, but not limited to, Si, Zn, and Sn. Activation of the C—X bond then occurs with subsequent transfer of X to a new carbon in the molecule, followed by the formation of C—Y. The activating group X is recycled by the construction of a final C—Z bond.

The work described herein arose from our attempts to prepare borane 3 from o-halostyrene 1 using a CuCl/dppbz catalyst (Table 1-1, entry 1). While none of the desired hydroboration was noted, due mainly to polymerization of the styrene, we observed small amounts of unexpected byproduct 2. Curious as to whether 2 might be obtained exclusively, we undertook an investigation of several mono- and bidentate ligands for CuCl (Table 1-1).

TABLE 1-1

Initial Ligand Screen.[a]

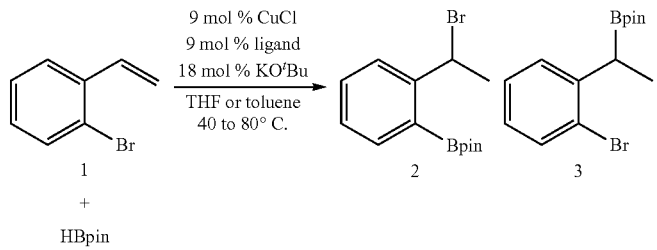

| entry[a] | ligand | 1 | 2 | 3 | entry | ligand | 1 | 2 | 3 |
|---|---|---|---|---|---|---|---|---|---|
| 1 | dppbz | <10% | <10% | 0% | 7 | dppb | 68% | 0% | 0% |
| 2 | PPh$_3$ | 50% | 0% | 0% | 8 | dppf | 0% | 0% | 0% |
| 3 | PCy$_3$ | 60% | 0% | 29% | 9 | phen | 94% | 0% | 0% |
| 4 | dppm | 51% | 0% | 41% | 10 | Xantphos | 1% | 0% | 72% |
| 5 | dppe | 30% | 0% | 0% | 11 | DPEphos | 42% | 0% | 0% |
| 6 | dppp | 19% | 0% | 0% | 12 | dCype | 0% | 70% | 0% |

[a]NMR yields using 1,1,1,2-tetrachloroethane as internal standard.

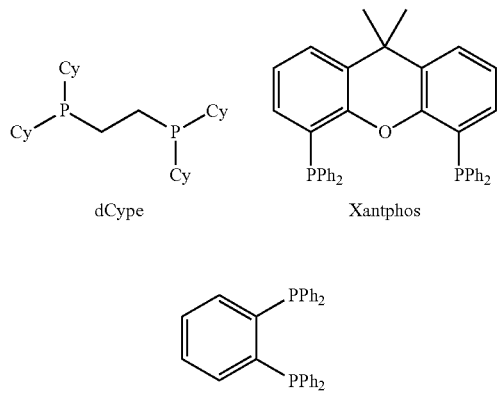

These preliminary studies revealed that neither monodentate phosphine ligands (entries 2, 3) nor electron-poor bidentate ligands (entries 4-8) were capable of promoting the desired reaction. Phenanthroline (entry 9) gave only recovered starting material. Interestingly, the trans-spanning Xantphos ligand (entry 10) gave exclusively the hydroboration product 3 in 72% yield, while a similar DPEphos ligand (entry 11) gave no 2 or 3. Finally, we found that the electron-rich and bulky bidentate phosphine ligand, bis(dicyclohexylphosphino)ethane (dCype, entry 12), exclusively promoted the desired 1,3-halogen migration.

Further reaction optimization was undertaken using the dCype ligand (Table 1-2). THF (entry 1) proved superior to toluene, CH$_2$Cl$_2$, Et$_2$O, CH$_3$CN, and CHCl$_3$ (entries 3-7), although dioxane (entry 2) gave similar results. Lowering the temperature to 40° C. (entry 8) did not increase the yield compared to entry 1, but improved the mass balance. Finally, scaling the reaction to 5 mmol (entry 9) reproducibly increased the yield to 94% of 2.

TABLE 1-2

Reaction Variations.[a]

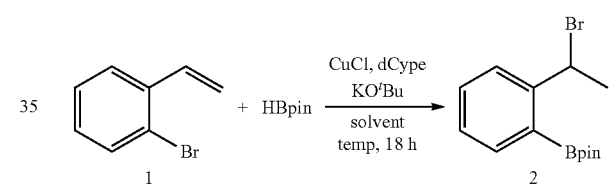

| entry | solvent | temp (° C.) | CuCl | dCype | KO$^t$Bu | 2 | 1 |
|---|---|---|---|---|---|---|---|
| 1[a] | THF | 70 | 9 | 9 | 18 | 73% | 2% |
| 2 | dioxane | 70 | 9 | 9 | 18 | 68% | 0% |
| 3 | toluene | 70 | 9 | 9 | 18 | 41% | 0% |
| 4 | CH$_2$Cl$_2$ | 70 | 9 | 9 | 18 | 54% | 6% |
| 5 | Et$_2$O | 70 | 9 | 9 | 18 | 40% | 3% |
| 6 | CH$_3$CN | 70 | 9 | 9 | 18 | 0% | 2% |
| 7 | CHCl$_3$ | 70 | 9 | 9 | 18 | 0% | 12% |
| 8 | THF | 40 | 9 | 9 | 18 | 60% | 27% |
| 9[b] | THF | 40 | 9 | 9 | 18 | 94% | 0% |

[a]NMR yields using 1,1,1,2-tetrachloroethane as the internal standard.
[b]Isolated yield from the reaction on a 5 mmol scale.

With optimized conditions in hand, we explored the scope of the reaction (Table 1-3). In general, 1,3-bromine migration was favored with a variety of substrates. However, placing electron withdrawing halogen groups meta to the olefin (entries 2, 3) diminished the 1,3-halogen migration and resulted in significant hydroboration. Other groups at this position favored transposition. Curiously, if a bromide group (entry 8) was placed para to the olefin, the hydrocupration did not occur at all.

TABLE 1-3

Substituent Effects on 1,3-Halogen Migration.[a]

[Reaction scheme: starting material 1, 4a-l (styrene with R_m, R_p substituents and ortho-Br) treated with 9% CuCl, 9% dCype, 18% KO^tBu, HBpin, THF 40° C., 18 h to give products 2, 5a-l (benzyl Br, Bpin on ring) and 3, 6a-l (benzyl Bpin, Br on ring)]

| entry | | $R_m$ | $R_p$ | | % yield | | | |
|---|---|---|---|---|---|---|---|---|
| 1 | 1 | H | H | 94% | 2 | 0% | 3 |
| 2 | 4a | Br | H | 57% | 5a | 31% | 6a |
| 3 | 4b | F | H | 49% | 5b | 28% | 6b |
| 4 | 4c | Ph | H | 73% | 5c | 0% | 6c |
| 5 | 4d | 1-Napth | H | 69% | 5d[a] | 0% | 6d |
| 6 | 4e | 4-MeOC$_6$H$_4$ | H | 67% | 5e | 0% | 6e |
| 7 | 4f | OMe | H | 87% | 5f | 0% | 6f |
| 8 | 4g | H | Br | 0% | 5g | 0% | 6g |
| 9 | 4h | H | F | 89% | 5h | 0% | 6h |
| 10 | 4i | H | Ph | 66% | 5i[a] | 12% | 6i |
| 11 | 4j | H | $^t$Bu | 65% | 5j[a] | 0% | 6j |
| 12 | 4k | H | OMe | 36% | 5k[a,b] | 0% | 6k |
| 13 | 4l[c] | H | H | 75% | 5l | 0% | 6l |

[a] The product was trapped with propargyl alcohol prior to isolation.
[b] 79% conversion.
[c] The starting material was 1-bromo-2-((1E)-prop-1-en-1-yl) benzene.

Neutral and electron-donating substituents F, Ph, $^t$Bu, and OMe (entries 9-12) para to the alkene yielded predominantly the 1,3-halogen migration products. For some of these cases, the benzyl bromide products were sensitive to elimination and were trapped with propargyl alcohol prior to isolation, illustrating the potential of this chemistry in cascade reactions to construct more complex compounds. Consistent with prior observations, the 4-methoxy substrate (entry 12) reacted slowly. Finally, substitution on the β carbon of the styrene (entry 13) was tolerated in the 1,3-halogen migration, as trans-β-methylstyrene 4l gave 5l in 75% yield. Although 2-chlorostyrenes underwent halogen transposition with poor conversions, it was found that 2-iodostyrene 4m did produce the transposed product (entry 14), although only partial conversion was observed. The sensitive benzyl iodide had to be trapped with propargyl alcohol to give 5m in moderate yield. The reactivity of 2-bromo-3-methylstyrene and 2-bromo-6-methylstyrene was also examined. While 1,3-halogen migration was observed, the conversion was low. Less bulky catalysts are being developed for sterically encumbered substrates.

The benzyl boronic esters that result from the typical hydroboration of styrenes are often utilized as synthons for benzylic carbanions. In contrast, the 1,3-halogen migration observed in our chemistry allows access to intermediates that are electrophilic at the benzylic carbon. Facile recycling of the activating group was demonstrated by transforming o-halostyrene 1 into a variety of benzyl-substituted boronic esters (Scheme 1-2). For example, propargyl and p-methoxybenzyl alcohols, aniline, and sodium azide were all suitable nucleophiles for reacting with the benzyl bromide to yield 7-9. These reactions represent formal Cu-catalyzed hydroalkoxylation and hydroaminations that are typically accomplished using more expensive precious metal catalysts including Pd, Rh, or Au.

Scheme 1-2. Recycling of the Activating Group.[a]

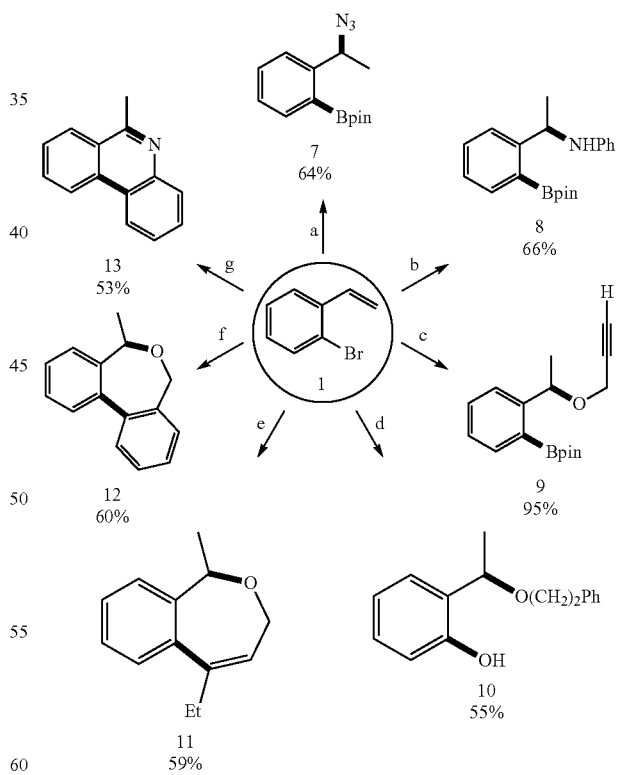

[a] Cu-catalyzed halogen transposition was followed by addition of the following: (a) 1.1 equiv of NaN$_3$, DMSO. (b) 1.2 equiv of aniline, 0.2 equiv of 18-crown-6, 1.5 equiv of K$_2$CO$_3$. (c) 1.2 equiv of propargyl alcohol, 0.2 equiv of 18-crown-6, 1.5 equiv of K$_2$CO$_3$. (d) Ph(CH$_2$)$_2$OH, 0.2 equiv of 18-crown-6, 1.0 equiv of $K_2CO_3$, then $H_2O_2$/NaOH. (e) (Z)-3-Iodopent-2-en-1-ol, 1.2 equiv of $K_2CO_3$, 0.2 equiv of 18-crown-6, then 10 mol % $PdCl_2dppf$, 3 equiv of $K_3PO_4.H_2O$, 9:1 DME:$H_2O$. (f) 2-Iodobenzyl alcohol, 1.2 equiv of $K_2CO_3$, 0.2 equiv of 18-crown-6, then 10 mol % $PdCl_2dppf$, 3 equiv of $K_3PO_4.H_2O$, 9:1 DME:$H_2O$. (g) 2-Iodoaniline, 0.2 equiv of 18-crown-6, 1.5 equiv of $K_2CO_3$, then 10 mol % $PdCl_2dppf$, 3 equiv of $K_3PO_4.H_2O$, 9:1 DME:$H_2O$, followed by $H_2O_2$.

In addition to functionalization at the benzylic carbon, the boronic ester can also be transformed into either a carbon-heteroatom or carbon-carbon bond. For example, treatment of o-halostyrene 1 under Cu catalysis, followed by reaction with 3-phenylpropan-1-ol and an oxidative workup using $H_2O_2$, yielded the phenol 10. Recycling the bromine activating group also provided a flexible platform for convergent syntheses of heterocycles. Tandem 1,3-halogen migration/functionalization/Suzuki couplings of 1 were accomplished using (Z)-3-iodopent-2-en-1-ol and 2-iodobenzyl alcohol to yield the heterocyclic dihydroxepins 11 and 12. Finally, halogen migration followed by reaction with 2-iodoaniline and subsequent Pd-catalyzed coupling/oxidation gave the biologically active phenanthridine core of 13.

Thus, with selection of appropriate starting materials, products of Formula (A) or (B) can be prepared:

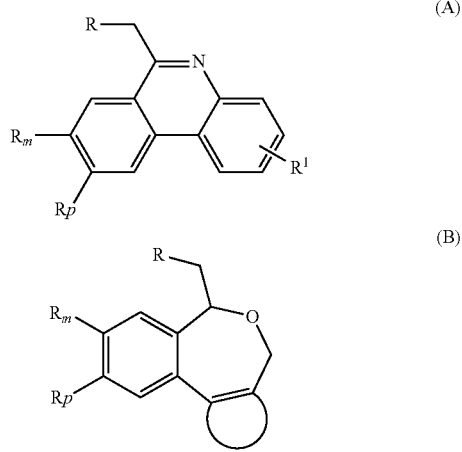

where R, $R^1$, $R_m$, and $R_p$ can be any suitable substituent or R groups as defined herein, and the ring on the oxygen heterocycle of Formula (B) can be any cycloalkyl, heterocycloalkyl, aryl, or heteroaryl ring.

We wanted to ensure that we were not observing direct borylation of the Ar—Br bond, followed by an unexpected bromination of the alkene. Examples of aryl bromides that undergo Cu-catalyzed borylation in the absence of a directing group have been reported, but these reactions are rare. In our case, when both 1,4-dibromobenzene and m-halostyrene 14 were subjected to the reaction conditions (eqs 1 and 2), no borylation of either C—Br bond was observed.

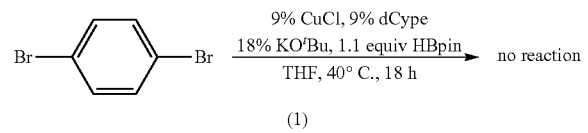

(1)

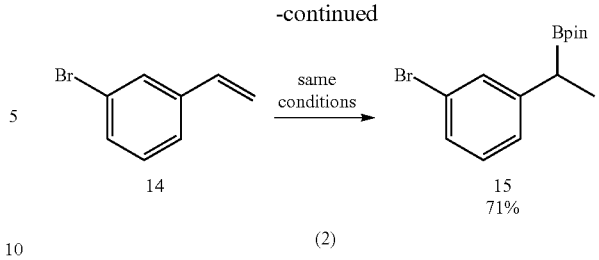

(2)

Subjecting the typical hydroboration product 3 to the reaction conditions also did not lead to 2, indicating direct borylation of 1 is not a likely reaction pathway.

We also demonstrated that the 1,3-halogen migration is likely an intramolecular process by performing a cross-over experiment using isotopically enriched [79]Br. The enriched aryl bromide 4f (Scheme 1-3) was prepared by reacting the tributylaryltin 16 with ~85% isotopically enriched $NH_4$[79]Br. After we ensured that the unlabeled styrenes 1 and 4f reacted at comparable rates, reaction of 4f in the presence of nonisotopically enriched 1 showed no additional incorporation of [79]Br into 2 or degradation of the [79/81]Br ratio in the conversion of 4f to 5f within statistical error.

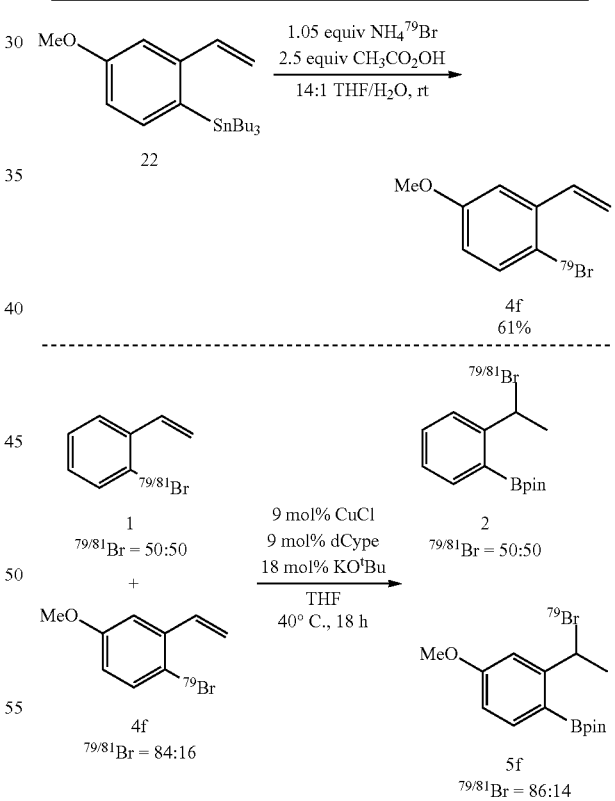

Scheme 1-3. Cross-Over Experiment Using Isotopically Enriched [79]Br.[a]

Thus, Cu(I) promotes a cascade 1,3-halogen migration/borylation/functionalization that proceeds under mild conditions to recycle the bromine activating group. The resulting benzyl bromide can be displaces with a wide variety of nucleophiles to provide amines, azides, ethers, cyclic ethers, amines, and the like. Prior to or after transformations involving the halide, a wide range of transformations can be carried out on the borane for the development of therapeutic intermediates and ligands for catalysis.

Abbreviations: dppbz, 1,2-bis(diphenylphosphanyl)benzene; PCy$_3$, tricyclohexylphosphine; dppm, diphenylphosphinomethane; dppe, 1,2-diphenylphosphinoethane; dppp, 1,3-diphenylphosphinopropane; dppb, 1,4-diphenylphosphino butane; dppf, diphenylphosphinoferrocene; phen, phenanthroline; Xantphos, 4,5-bis(diphenylphosphino)-9,9-dimethylxanthene; DPEphos, bis(2-diphenylphosphino phenyl)ether; dCype, 1,2-bis(dicyclohexylphosphino)ethane.

Example 2

Copper-Catalyzed Enantioselective Transfer of Bromine via 1,3-Halogen Migration In a typical coupling reaction, one new bond is formed at the expense of two functional groups as well as the generation of a waste product (Scheme 2-1, top). In the newly developed approach, all of the atoms from both coupling partners are incorporated into the final product via a 1,3-migration of the catalyst (Scheme 2-1, bottom).

Scheme 2-1. New mode of arene functionalization vs. traditional cross-coupling approach.

Typical approach:

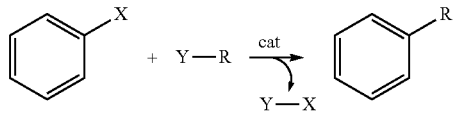

Halogenation via 1,3-Migration:

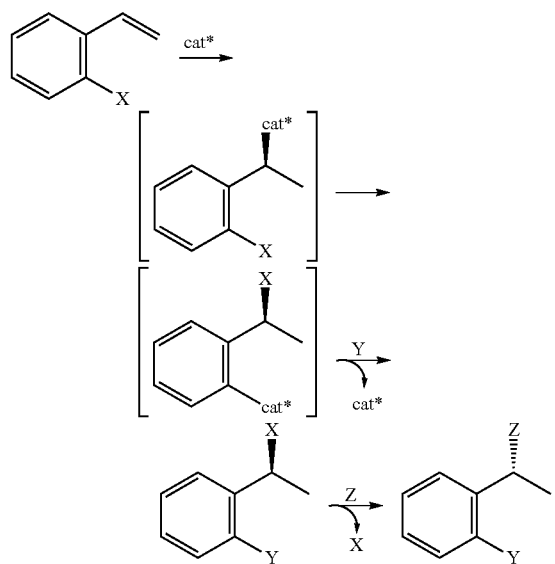

X═Cl, Br, I
Z═nucleophiles such as azide, amines, alkoxides, thiols, phosphines, carbanions (e.g., malonates, enolates, etc.), and the like.
The phenyl group can also be substituted by 1-4 R groups, as in Formula (I) and Scheme 1-1.

In this transformation, the catalyst first adds across an olefin to generate a benzyl metal catalytic species. This intermediate then rearranges, breaking the aryl C—X bond (X═I, Br, or Cl) to form a benzyl C—X bond. The aryl catalyst species then forms a new aryl C—Y bond with a coupling partner. The benzyl C—X can then be displaced in the same pot with a nucleophile, Z. This new mode of reactivity provided a unique opportunity to set the stereochemistry of a benzyl bromide in a catalytic fashion resulting in a valuable product. The enantio-enriched halide can then be displaced in an S$_N$2 fashion, allowing for rapid construction of complex motifs in one reaction vessel.

The work described herein details our efforts to prepare bromide 2 (Table 2-1.1 and 2-1.2) in an enantioselective fashion. Based upon our previous work, we focused our attention on several chiral bidentate phosphine ligands for CuCl (Table 2-1.1). In general, BINAP-derived ligands (entries 1-6) all gave good conversion, but enantio-induction was highly variable. Ligands with larger R groups on phosphorous (entries 1, 2, 4 and 6) tended to afford better ee's than ligands with smaller R groups on phosphorous (entries 3 and 5). The DIPAMP ligand gave moderate conversion and poor ee (entry 7). A series of ligands with a defined bite angle enforced by a benzene ring gave moderate to excellent conversions (entries 8-10). Me-DuPhos gave a mixture of the desired product, 2, and the benzyl boronic ester (entry 8), however, switching the R group to the bulkier isopropyl provided the desired product in moderate ee (entry 9). Switching to a ligand that is chiral at phosphorous gave only moderate conversion and poor ee (entry 10). The Josiphos ligand derivative gave excellent conversion, but poor ee (entry 11). We then began an investigation of bis-phopholane ligands (entries 12-14). Unfortunately, the methyl derivative gave the benzyl boronic ester exclusively (entry 12), but the isopropyl derivative gave the desired product in good conversion, but in low enantio-induction (entry 13). Finally, the phenyl derivative gave both high conversion and good enantio-selectivity (entry 14). Together, this indicates that an electron-rich, bulky, bidentate phosphine ligand is helpful not only to promote the reaction but also to obtain high ee.

TABLE 2-1.1

Initial ligand screen.

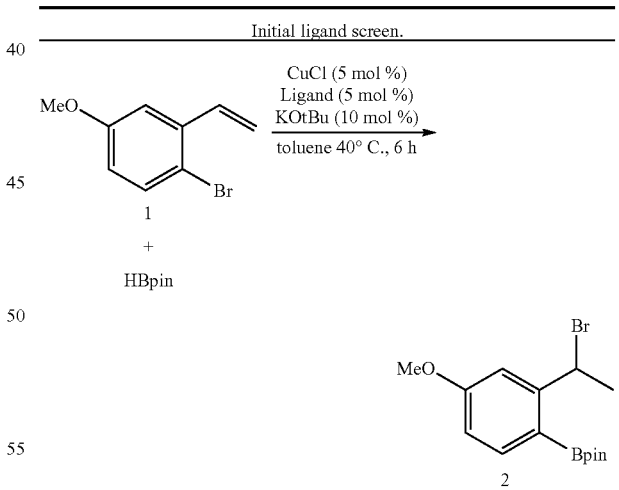

| entry | ligand | conv. | ee |
|---|---|---|---|
| 1 | (R)-T-BINAP | 87 | 68 |
| 2 | (R)-DM-BINAP | 100 | 72 |
| 3 | SEGPHOS | 90 | 46 |
| 4 | DTBM-SegPhos | 84 | 72 |
| 5 | S-Tunephos | 92 | 3 |
| 6 | BINAPINE | 100 | 66 |
| 7 | (S,S)-DIPAMP | 69 | 10 |
| 8 | Me-DuPhos | 100 | —[a] |
| 9 | $^i$Pr-DuPhos | 95 | 72 |

TABLE 2-1.1-continued

Initial ligand screen.

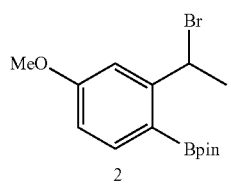

| entry | ligand | conv. | ee |
|---|---|---|---|
| 10 | BenzP* | 73 | 31 |
| 11 | Josiphos SL-J003-1 | 100 | 38 |
| 12 | (S,S)-Me-BPE | 100 | —[b] |
| 13 | (S,S)-$^i$Pr-BPE | 62 | 18 |
| 14 | (S,S)-Ph-BPE | 97 | 80 |

[a] 3:2 ratio of 2 and benzyl boronic ester
[b] 100% benzyl boronic ester

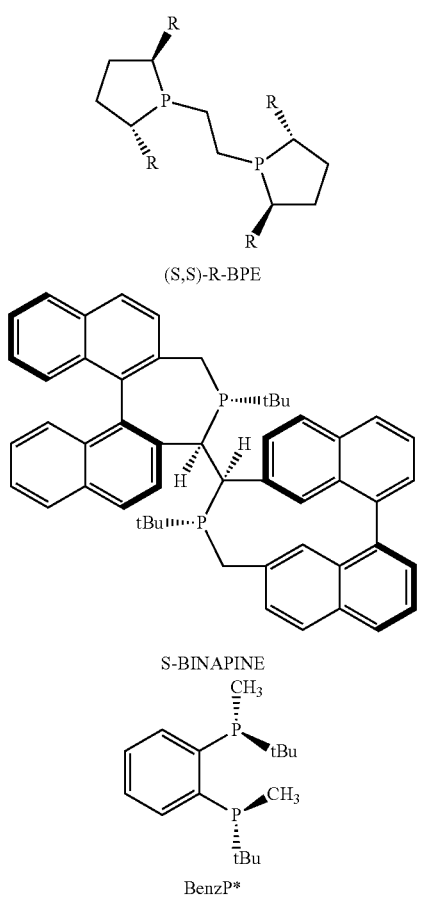

(S,S)-R-BPE

S-BINAPINE

BenzP*

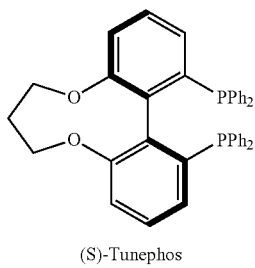

(S)-Tunephos

Further studies were performed by exploring a series of chiral bidentate phosphine ligands for CuCl (Table 2-1.2). While three ligands (entries 2, 4 and 14) gave ee's greater than 60% at 50° C., (S,S)-Ph-BPE (entry 14) produced the highest ee's by far.

TABLE 2-1.2

Preliminary investigation of ligands for enantioselective halogenation.

2: X = Br, Y = Bpin
3: X = Bpin, Y = Br

| entry | ligand[a] | 1 | 2 | 3 | ee |
|---|---|---|---|---|---|
| 1 | (R)-T-BINAP | 23 | 17 | 0 | 54 |
| 2 | (R)-DM-BINAP | 18 | 33 | 0 | 66 |
| 3 | SEGPHOS | 12 | 29 | 0 | 30 |
| 4 | DTBM-SegPhos | 15 | 8 | 0 | 62 |
| 5 | (S)-TunePhos | 8 | 46 | 0 | −41 |
| 6 | Tangphos | 22 | 17 | 31 | n.d. |
| 7 | DIPAMP | 20 | 17 | 0 | 6 |
| 8 | (R,R)-Me-DuPhos | 8 | 23 | 0 | 21 |
| 9 | (S,S)-iPr-DuPhos | 23 | 0 | 0 | n.d. |
| 10 | (R)-BenzP* | 36 | 21 | 0 | −29 |
| 11 | (S)-Josiphos SL-J003-1 | 0 | 82 | 0 | 37 |
| 12 | (S,S)-Me-BPE | 19 | 0 | 0 | n.d. |
| 13 | (R,R)-iPr-BPE | 13 | 17 | 0 | −9 |
| 14 | (S,S)-Ph-BPE | 14 | 34 | 0 | 78 |

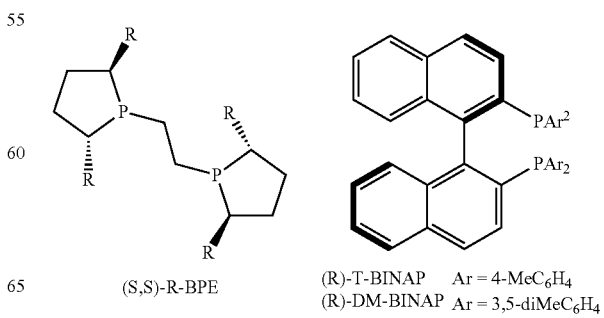

(S,S)-R-BPE (R)-T-BINAP  Ar = 4-MeC$_6$H$_4$
(R)-DM-BINAP Ar = 3,5-diMeC$_6$H$_4$

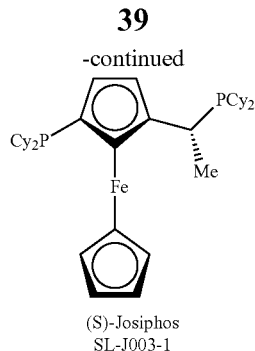

(S)-Josiphos
SL-J003-1

Further reaction innovation was achieved with the Ph-BPE ligand (Tables 2-2.1 and 2-2.2). Dropping the temperature of the reaction increased ee of the reaction appreciably (Table 2-2.1; entry 1), but continuing to lower the temperature resulted in poor conversion (Table 2-2.1; entries 2 and 3). Nonpolar solvents such as cyclohexane (Table 2-2.1; entry 4) gave good ee, but the conversion was again low. Performing the reaction in benzene (Table 2-2.1; entry 5) resulted in excellent conversion, but only modest ee. The migration reaction was operative in ethereal solvents (Table 2-2.1; entries 6-8), with non-polar diethyl ether performing the best with decent conversion and good ee. As the polarity of the ether solvents increased from diethyl ether to methyl tert-butyl ether to dimethyl ethylene glycol, both conversion and ee tended to decrease. Halogenated solvents (Table 2-2.1; entries 9 and 10) performed poorly with both low conversion and poor ee. The conditions in entry 1 seemed to be the best for both good conversion and good ee.

TABLE 2-2.1

Reaction variations.

| entry | solvent | temp. | conv. | ee |
|---|---|---|---|---|
| 1 | toluene | 25° C. | 94 | 86 |
| 2 | toluene | 0° C. | 50 | 93 |
| 3 | cyclohexane | 25° C. | 64 | 92 |
| 4 | benzene | 25° C. | 95 | 79 |
| 5 | Et$_2$O | 25° C. | 80 | 90 |
| 6 | MTBE | 25° C. | 79 | 87 |
| 7 | glyme | 25° C. | 67 | 64 |
| 8 | DCM | 25° C. | 53 | 25 |
| 9 | C$_6$F$_6$ | 25° C. | 51 | 65 |

Further reaction optimization focused on variations in the temperature, concentration and the base (Table 2-2.2). Whereas the yield was poor at room temperature, the ee was improved compared to running the reaction at 50° C. (Table 2-2.2; entry 1). Decreasing the concentration from 0.5 M to 0.1 M significantly improved the mass balance by decreasing the rate of ATRP (Table 2-2.2; entry 2), a major side reaction. Higher catalyst loadings did not increase conversion, but switching the additive from KOtBu to NaOtBu increased the yield to 75% at the expense of ee (Table 2-2.2; entries 3, 4). The best results were obtained by lowering the reaction temperature to 0° C. in the presence of NaOtBu as the base (Table 2-2.2; entry 5).

TABLE 2-2.2

Further optimization of the asymmetric 1,3-halogenation migration.[a]

| entry | temp (° C.) | MO$^t$Bu | loading | [conc] | 1[a] | 2 | ee |
|---|---|---|---|---|---|---|---|
| 1 | 25 | KOtBu | 5% | 0.5M | 16 | 46 | 86 |
| 2 | 25 | KOtBu | 5% | 0.1M | 52 | 34 | 83 |
| 3 | 25 | KOtBu | 10% | 0.1M | 41 | 38 | 85 |
| 4 | 25 | NaOtBu | 10% | 0.1M | 13 | 75 | 75 |
| 5 | 0 | NaOtBu | 10% | 0.1M | <10 | 73[b] | 96 |

[a]NMR yields determined using 1,1,1,2-tetrachloroethane as the internal standard.
[b]Isolated yield.

The scope of the reaction was explored to provide further innovation for the new methods (Tables 2-3.1 and 2-3.2). Changing the OMe group to a bulkier OiPr group resulted in a lower yield but excellent ee (Table 2-3.2; entry 2). Substitution of the Br with I diminished the ee to 66% (Table 2-3.2; entry 3), due to the sensitive nature of the benzyl iodide product. The parent 2-bromostyrene still exhibited good ee (Table 2-3.2; entry 4), but the yield was significantly lower compared to the 94% obtained using the racemic version of the catalyst. Substitution at the β-carbon of the styrene, as well as a fluorine at C5, were tolerated (Table 2-3.2; entry 5), although the ee values were lower.

TABLE 2-3.1

Scope of asymmetric 1,3-halogen migration.

R₁–Ar(R₂)(Br)–CH=CH₂ + HBpin → CuCl (5 mol %), (S,S)-Ph-BPE (5 mol %), KOtBu (10 mol %), toluene, 25° C., 6 h → product with Br and Bpin

| entry | R₁  | R₂ | ee |
|-------|-----|----|-----|
| 1     | H   | H  | 91 |
| 2     | OMe | H  | 94 |
| 3     | Ph  | H  | 83 |

TABLE 2.3.2

Selected substrate scope.

1, 4a-e + HBpin → 10 mol % CuCl, 10 mol % (S,S)-Ph-BPE, 20 mol % NaO$^t$Bu, toluene, 0° C., 18 h → 2, 5a-e

| entry | substrate | yield | ee |
|-------|-----------|-------|-----|
| 1 | MeO-aryl-Br (1) | 73% 2 | 92 |
| 2 | $^i$PrO-aryl-Br (4a) | 53% 5a | >99 |
| 3 | MeO-aryl-I (4b) | 71%$^a$ 5b | 66 |
| 4 | aryl-Br (4c) | 28% 5c | 84 |
| 5 | aryl-Br with propenyl (4d) | 40% 5d | 89 |
| 6 | F-aryl-Br (4e) | 38% 5e | 81 |

$^a$Trapped with LiSePh before isolation.

Other examples of $R_1$ and $R^2$ groups include substituted aryls such as p-methoxyphenyl, other aryls including naphthyl, and halogens such as fluorine.

To obtain a better understanding of the factors controlling the reactivity, density functional theory (DFT) calculations were carried out. Rather than simply targeting an overall reaction coordinate, three major features of a set of "training" substrates and products were considered with the goal of developing a simple, empirical equation capable of approximating relative behavior of o-bromostyrenes in the 1,3-halogen migration to establish a trend in reactivity. Several experimental results were used to generate an equation (Table 3) that matched experiment to within 10% (Table 4). We hypothesized that greater electron density at the bromine-bearing carbon (carbon labelled γ) would enhance the rate of the 1,3-halogen migration reaction as this carbon likely needs to bind to the Lewis acidic copper during the course of the reaction. The major ATRP side reaction was proposed to be favored by factors that promote or stabilize the formation of a benzyl radical (represented by ΔΔG). Finally, the steric bulk of the (S,S)-Ph-BPE catalyst is greater than that of the dCype ligand used in our racemic studies; thus, a steric factor was also included in our studies (represented by χ). For the substrates used to generate the equation, χ and ΔΔG contributed nearly equally, whereas γ contributed approximately twice that of either χ or ΔΔG. Each of these factors were parameterized from optimized structures (B3LYP/6-311++G (2d, p)) (A. D. Becke, *J. Chem. Phys.* 1993, 98, 5648-5652) using Gaussian 09 (see A. D. McLean, G. S. Chandler, *J. Chem. Phys.* 1980, 72, 5639-5648; K. Raghavachari, J. S. Binkley, R. Seeger, J. A. Pople, *J. Chem. Phys.* 1980, 72, 650-654; R. C. Binning, L. A. Curtiss, *J. Comp. Chem.* 1990, 11, 1206-1216; M. P. McGarth, L. Radom, *J. Chem. Phys.* 1991, 94, 511-516; (e) L. A. Curtiss, M. P. McGarth, J.-P. Blaudeau, N. E. Davis, R. C. Binning Jr., L. Radom, *J. Chem. Phys.* 1995, 103, 6104-6113) and NBO (E. D. Glendening, J. K. Badenhoop, A. E. Reed, J. E. Carpenter, J. A. Bohmann, C. M. Morales, C. R. Landis, and F. Weinhold (Theoretical Chemistry Institute, University of Wisconsin, Madison, Wis., 2013); http://nbo6.chem.wisc.edu/).

TABLE 3

Yield trend for asymmetric 1,3-halogen migration.

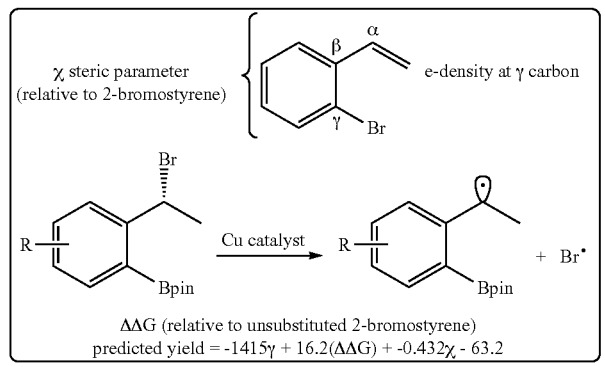

| yield | substrate | actual[a] | calculated | γ | ΔΔG | χ |
|---|---|---|---|---|---|---|
| 1 | 4c | 35% | 34% | −0.069 | 0.00 | 0.00 |
| 2 | 1 | 73% | 65% | −0.095 | 0.21 | 22.2 |
| 3 | 4e | 37% | 46% | −0.087 | −0.59 | 10.3 |
| 4 | 4a | 54% | 56% | −0.097 | 0.37 | 55.8 |

[a]NMR yields determined using 1,1,1,2-tetrachloroethane as the internal standard.

TABLE 4

Comparison of Calculated and Experimental Yields.[a]

| Entry | Substrate | Calculcated Yield | Experimental Yield[a] |
|---|---|---|---|
| "Training" Set: | | | |
| 1 | H | 34 | 35 |
| 2 | 5-OMe | 65 | 73 |
| 3 | 5-F | 46 | 37 |
| 4 | 4-F | 12 | 14 |
| 5 | 5-$^t$Bu | 24 | 25 |
| 6 | 4-$^t$Bu | 13 | 4 |
| 7 | 4-Ph | 0.4 | 7 |
| 8 | 5-pyrryl | 23 | 24 |
| 9 | 5-O$^i$Pr | 56 | 54 |
| 10 | β-Me | 39 | 40 |
| Control Group: | | | |
| 11 | 5-OBz | 15 | 8 |
| 12 | 5-OTBS | 22 | 21 |
| 13 | 5-Br | 25 | 16 |
| 14 | 6-F | 18 | 9 |

[a]NMR yields determined using 1,1,1,2-tetrachloroethane as the internal standard.

TABLE 5

Testing the predictive model for asymmetric 1,3-halogen migration.

| entry | substrate | calculated yield | yield | | ee |
|---|---|---|---|---|---|
| 1 | MeS– (4f) | 10% | 13%[a] | 5f | n.d. |
| 2 | Me– (4g) | 36% | 30%[b] | 5g | 89 |
| 3 | EtO– (4h) | 58% | 57%[b] | 5h | 89 |
| 4 | MeO– (4i) | 63% | 50%[b] | 5i | 93 |
| 5 | MeO– (4j) | quant. | 50%[b] | 5j | 70 |
| 6 | F– (4k) | quant. | 65%[a] | 5k | 81 |

[a]NMR yields determined using 1,1,1,2-tetrachloroethane as the internal standard.
[b]Isolated yield.

This simple equation indicates that relative to 2-bromostyrene, (Table 3; entry 1), increasing the electron density at the C—Br carbon results in increased yields. However, if the ΔΔG of benzyl radical formation is negative compared to 2-bromostyrene (entry 3), the yield is adversely affected. Finally, the presence of large R groups (entry 4) is also detrimental to the yield.

The equation was then tested on substrates different from those used to generate the equation to confirm whether or not the trend was an artifact of data fitting. For example, a SMe group in the position para to the Br might be expected to exhibit similar reactivity to an OMe group, based on both electronic and steric arguments. However, the calculated yield for this substrate was poor, which was indeed the case (Table 5; entry 1). Addition of a weakly donating group in the C5 position did not result in significant improvement in yield (Table 5; entry 2). Installation of a OEt group at the C5 position was predicted to give 5 h in 58% yield, which was comparable to the observed yield of 57% (Table 5; entry 3). Although substitution on the alkene resulted in slightly lower yields than expected, the observed and calculated yields were reasonably comparable (Table 5; entry 4). Moving steric bulk closer to one of the reactive sites should cause the equation to over-estimate the yield since none of the substrates used to create the equation have steric bulk ortho to a reactive site. Indeed, our equation predicted that placing OMe at C3 of 4i would result in a quantitative yield while the yield of 5i (Table 5; entry 5) was 50%. Installing F at C3 resulted in a lower-than-predicted quantitative yield, but is still one of the highest yields observed for this reaction (Table 5; entry 6).

Transformation of the benzyl halide resulting from asymmetric 1,3-migration into a variety of enantio-enriched benzyl substituted boronic esters was performed to demonstrate the facile recycling of the bromide activating group (Schemes 2-2.1 and 2-2.2). Additionally or alternatively, the benzylbromide boronate can be used as a substrate in Suzuki reactions, Cham-Lam coupling, and cross-coupling with oxygen-containing or phosphorus containing partners.

Scheme 2-2.1 Recycling of the activating group and concomitant bromide displacement products.

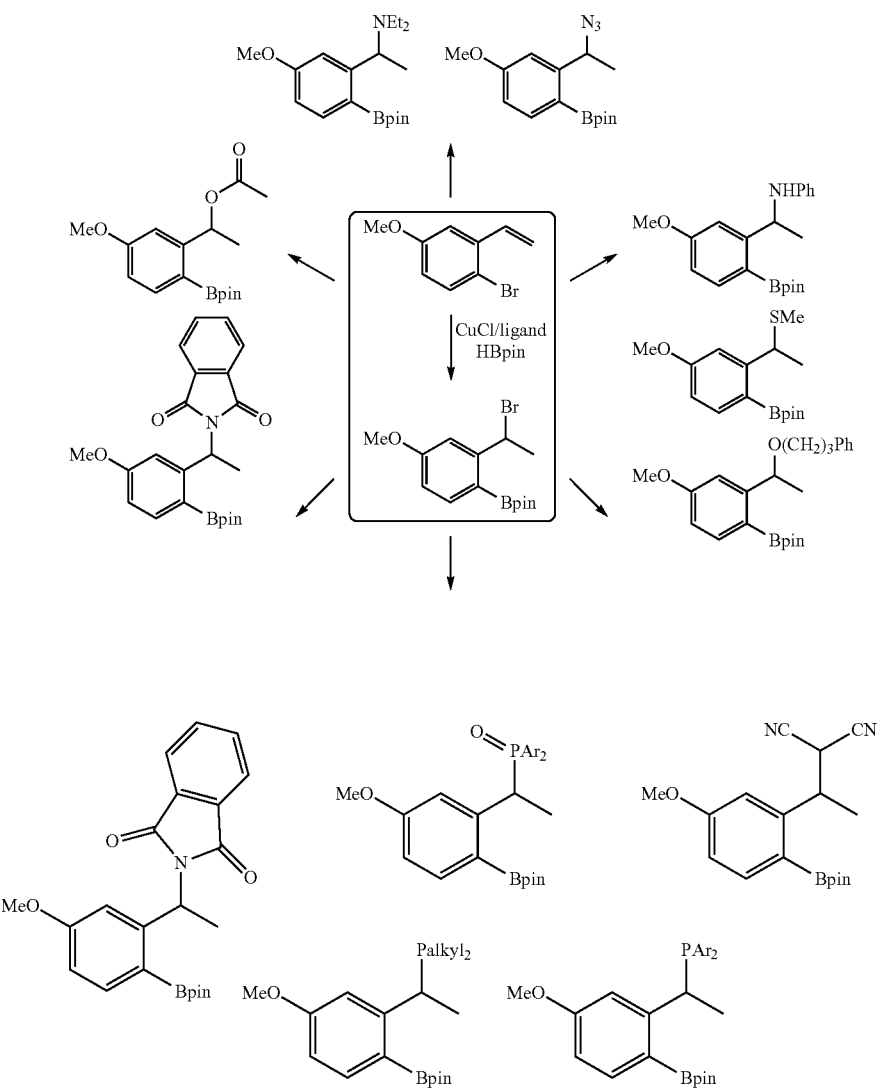

Scheme 2-2.2 Functionalization of the chiral benzyl bromide.

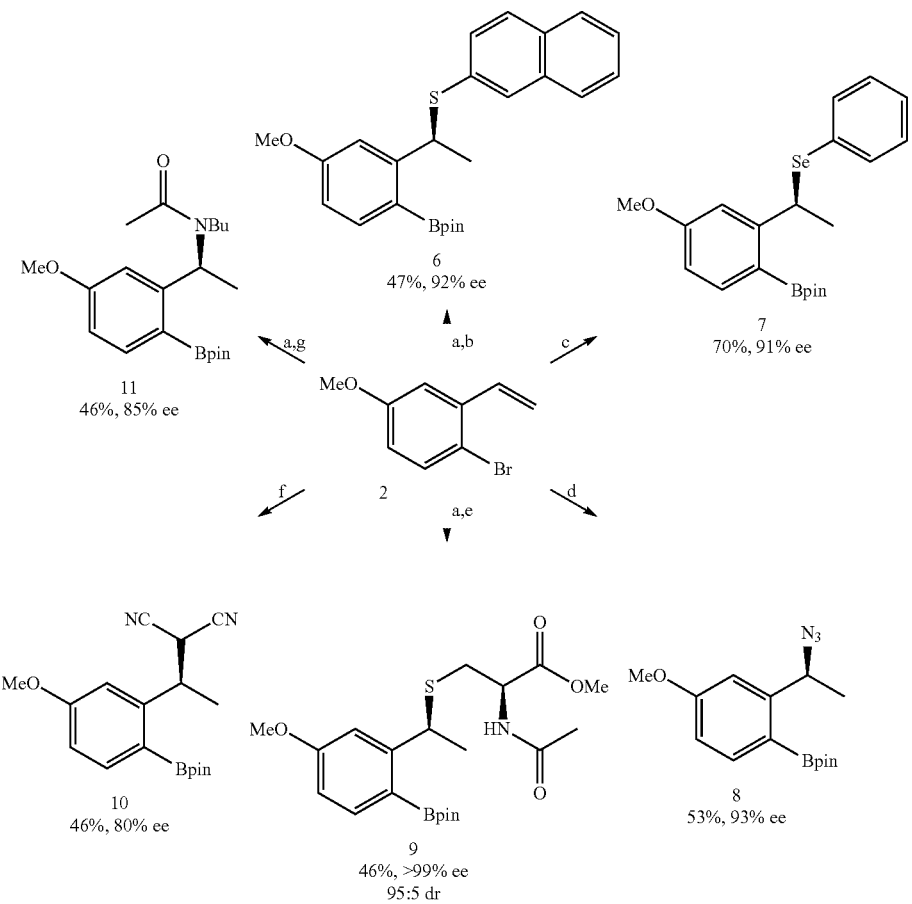

(a) Standard asymmetric halogen migration conditions and then the solvent was removed. (b) 1.5 equiv 2-naphthalenethiol, 2.5 equiv K$_2$CO$_3$, DMF, 1 h, RT. (c) Standard asymmetric halogen migration conditions and then 3 equiv of LiSePh in THF was added. (d) Standard asymmetric conditions and then 3.0 equiv TMSN$_3$, 3 equiv CsF, DMSO, 40° C., 16 h. (e) 1.5 equiv N-acetyl cysteine methyl ester, 2.5 equiv K$_2$CO$_3$, DMSO, 40° C., 3 h. (f) Standard asymmetric conditions and then 3.0 equiv lithium malononitrile in THF. (g) 3 equiv butylamine, 5 equiv K$_2$CO$_3$, DMF, 40° C., 1 h then 5 equiv Ac$_2$O, 40° C., 1 h.

The reaction products can be used as intermediates for the preparation of other useful compounds including novel chiral ligands. Copper(I) thus promotes a cascade 1,3-halogen migration/borylation/functionalization that proceeds under mild conditions to recycle the bromine activating group with good enantiocontrol. In addition to bromine, other halogens including iodine and chloride can serves as transferrable activating groups.

The mode of stereo-induction was also studied. Subjecting 2-chlorostyrene, which is sterically and electronically similar to 2-bromostyrene, but does not undergo migration, produces a benzyl boronic ester with the opposite sense of chirality:

(1)

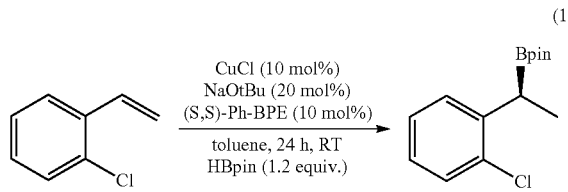

The addition of the copper-hydride to the olefin was investigated using structures optimized with Gaussian 09 (B3LYP/6-311G* for H, C, P, and Br and a LANL2TZ+ basis utilizing an electric core potential for Cu[17]) and each transition state was checked for one negative vibrational mode. Asymmetric additions of copper-hydrides to olefins are often invoked and this study did indeed show that the pathway that leads to the (S)-benzyl copper species is lower in energy than the one that leads to the (R)-benzyl copper.

The absolute stereochemistry of the benzyl-bromide product was determined by X-ray crystallography (data not shown). The (S,S)-Ph-BPE yielded the (R) configuration of the benzyl bromide.

Thus, this example shows that a Cu(I) catalyst supported by a (S,S)-Ph-BPE ligand promotes a cascade 1,3-halogen migration/borylation reaction that proceeds under mild conditions and results in a formal enantioselective addition of HBr across a carbon-carbon double bond.

Example 3

Chiral Ligand Preparation

The hydrobromination methods described herein can be used to prepare both novel and commercially available ligands. The hydrobromination can be rendered enantioselective by use of an electron-rich, bulky, bidentate phosphine ligand such as (S,S)-Ph-BPE:

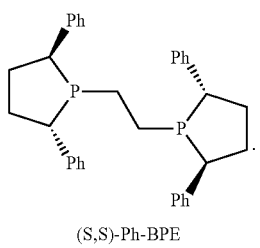 [SMILES: c1ccc([C@@H]2CC[C@@H](c3ccccc3)P2CCP2[C@H](c3ccccc3)CC[C@H]2c2ccccc2)cc1]

(S,S)-Ph-BPE

One commercially available chiral ligand that can be prepared using the methods described herein is (S)-1-(2-(diphenylphosphino)phenyl)ethanamine ((S,S)-Ph-BPE). The sequence requires only three steps to provide the commercially valuable ligand, as shown below in Scheme 3-1.

Scheme 3-1. Preparation of (S)-1-(2(diphenylphosphino)phenyl)ethanamine.

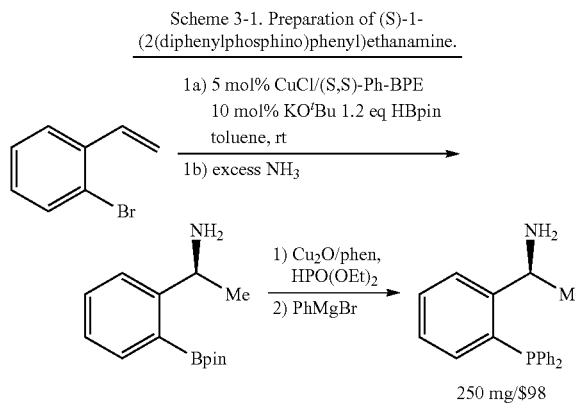

250 mg/$98

The ligand can be easily diversified, for example, by reactions at the amine (e.g., alkylations, conjugations, protections, etc.), at the methyl or phenyl ring (e.g., by selecting an alternative starting material with various substitution patterns), or at the phosphine, such as by using any of a wide variety of Grignard reagents. Various Grignard and related organometallic reagents and their methods of use are described by, for example, U.S. Patent Publication No. 2005/0124808 (Miller). Bidentate ligands can be prepared by using a bis-functionalized alkylating agent such as a dihaloalkane (e.g., an optionally substituted, optionally interrupted branched, cyclic, or straight chain $(C_1-C_{20})$alkylene substituted by two halogens selected from chlorine, bromine, iodine, and combinations thereof. Specific suitable examples include 1,2-dibromoethane, 1,3-dibromopropane, 1,4-dibromobutane, 1,5-dibromopentane, and the like.

Another commercially available chiral ligand that can be prepared using the methods disclosed herein is (R)-8-(diphenylphosphino)-1,2,3,4-tetrahydronaphthalen-1-amine. The sequence requires only two steps to provide the commercially valuable ligand (Scheme 3-2 below).

Scheme 3-2. Preparation of (R)-8-(diphenylphosphino)-1,2,3,4-tetrahydronaphthalen-1-amines.

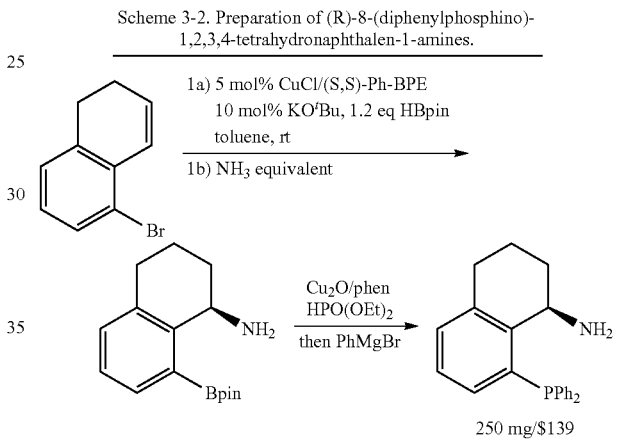

250 mg/$139

The tetrahydronaphthalenamine ligand can also be readily diversified at the amine and phosphine groups to provide other useful ligands.

Binapine is a useful, although expensive chiral ligand (~$132/100 mg). Binapine derivatives can be readily accessed using the methods described herein. For example, a dibenzyl binapine derivative can be prepared in five steps as illustrated in Scheme 3-3 below.

Scheme 3-3. Preparation of a dibenzyl binapine ligand.

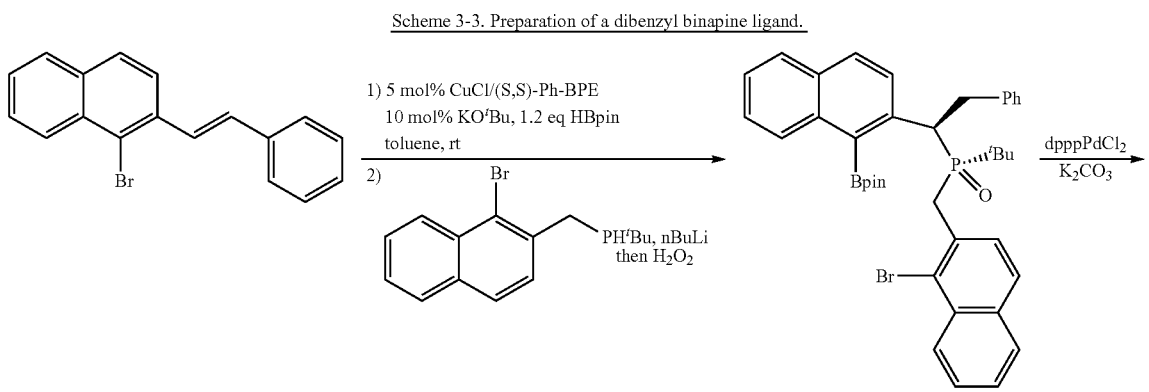

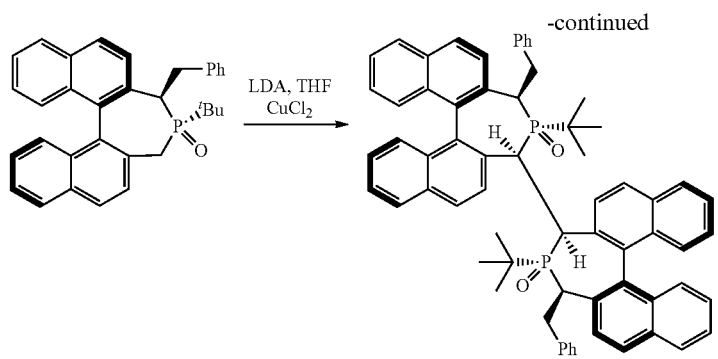
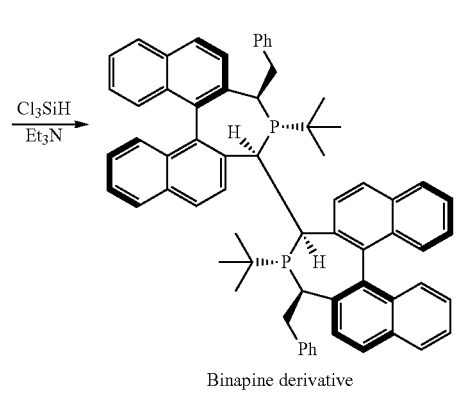

Binapine derivative

Other binapine derivatives can be easily prepared by initiating the sequence with phenyl substituents, or by employing groups other than tert-butyl on the phosphine coupling partner, such as methyl, ethyl, iso-propyl, iso-butyl, and phenyl, each optionally substituted. Additionally, the naphthyl groups can also be optionally substituted (e.g., at the 3, 4, 5, 6, 7, and/or 8 positions), for example with a variety of electron donating groups or electron withdrawing groups. Examples of electron donating groups include alkyls, alkoxides, heteroaryls, heterocycles, and amines. Examples of electron withdrawing groups include halogens (e.g., F), nitrile, and nitro groups.

Another group of useful but expensive chiral ligands are the DuanPhos ligands ($113/100 mg). DuanPhos derivatives can be prepared in five steps using the methods described herein and relevant transformations as illustrated below in Scheme 3-4.

Scheme 3-4. Preparation of DuanPhos ligands.

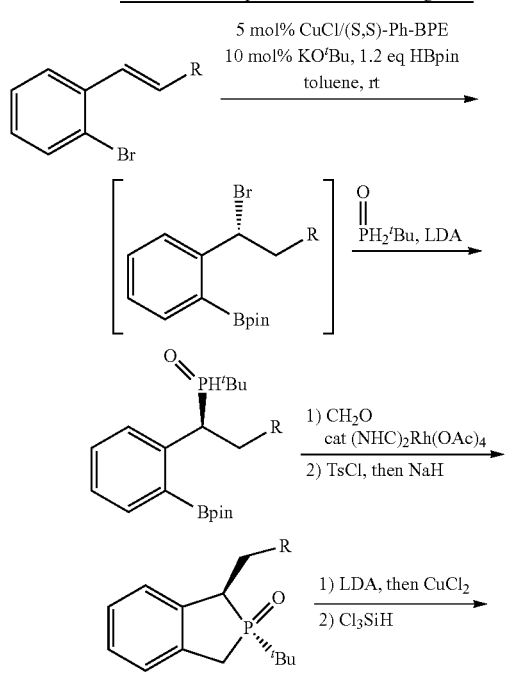

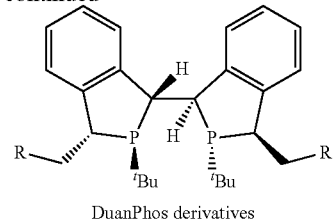

DuanPhos derivatives

R=alkyl, aryl, cycloalkyl, heterocycle, heteroaryl, —(CH$_2$)$_n$PR'$_2$, —(CH$_2$)$_n$NR'$_2$, —(CH$_2$)$_n$OR', where n is 1-12 and R' is optionally substituted alkyl, aryl, cycloalkyl, heterocycle, heteroaryl, or another R group or substituent as described herein.

Other DuanPhos derivatives can be prepared by varying the R group of the styrene-based starting material, and/or by using phosphine groups other than tert-butyl as a substituent on the phosphonate component.

While specific embodiments have been described above with reference to the disclosed embodiments and examples, such embodiments are only illustrative and do not limit the scope of the attached claims. Changes and modifications can be made in accordance with ordinary skill in the art without departing from the disclosure in its broader aspects as defined in the following claims.

All publications, patents, and patent documents are incorporated by reference herein, as though individually incorporated by reference. No limitations inconsistent with this disclosure are to be understood therefrom. The methods, compounds, catalyst, reagents, solvents, etc., have been described with reference to various specific and preferred embodiments and techniques. However, it should be understood that many variations and modifications may be made while remaining within the spirit and scope of the attached claims.

What is claimed is:

1. A method to functionalize an arene comprising contacting an optionally substituted o-halostyrene with a hydroborane in the presence of an effective amount of copper(I), a base, and an electron-rich bidentate phosphine ligand, resulting in a 1,3-halogen migration of the o-halo group to the benzyl position resulting in hydrohalogenation and hydroboration at the position previously held by the o-halo group, to provide a compound that is both a benzyl halide and an aryl boronic ester.

2. The method of claim 1, comprising displacing the benzylic halogen with a heteroatom nucleophile or a carbon nucleophile.

3. The method of claim 1, wherein the copper(I) is formed from CuCl, and the base is an alkali metal alkoxide.

4. A method to induce a 1,3-halogen a migration comprising contacting a compound of Formula (I):

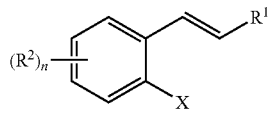

wherein
X is Cl, Br, or I;
R$^1$ is H, alkyl, aryl, heteroaryl, or cycloalkyl;
R$^2$ is H, halo, alkyl, alkoxy, aryl, or heteroaryl; and
n is 0, 1, 2, 3, or 4;
with a hydroborane in the presence of an effective amount of copper(I), a base, and an electron-rich bidentate phosphine ligand, to provide a compound of Formula (II):

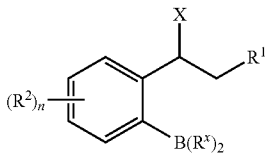

wherein each R$^x$ is independently a boron ligand or both R$^x$ groups together form a bidentate boron ligand.

5. The method of claim 4, wherein the electron-rich bidentate phosphine ligand is 1,2-bis(dicyclohexylphosphino)ethane ("dCype").

6. The method of claim 4, comprising displacing the benzylic halogen with a heteroatom nucleophile or a carbon nucleophile.

7. The method of claim 4, wherein the copper(I) is formed from CuCl, and the base is an alkali metal alkoxide.

8. A method to enantioselectively induce a 1,3-halogen a migration comprising contacting a compound of Formula (I):

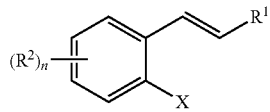

wherein
X is Cl, Br, or I;
R$^1$ is H, alkyl, aryl, heteroaryl, or cycloalkyl;
R$^2$ is H, halo, alkyl, alkoxy, aryl, or heteroaryl; and
n is 0, 1, 2, 3, or 4;
with a hydroborane in the presence of an effective amount of copper(I), a base, and a chiral electron-rich bidentate phosphine ligand, to provide an enantioenriched compound of Formula (II):

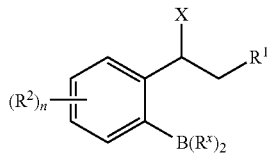

wherein each R$^x$ is independently a boron ligand or both R$^x$ groups together form a bidentate boron ligand.

9. The method of claim 8, wherein the chiral electron-rich bidentate phosphine ligand is (S)-1-(2-(diphenylphosphino)phenyl)ethanamine ("(S,S)-Ph-BPE").

10. The method of claim 8, comprising displacing the benzylic halogen with a heteroatom nucleophile or a carbon nucleophile.

11. The method of claim 8, wherein the copper(I) is formed from CuCl, and the base is an alkali metal alkoxide.

12. A method for preparing a chiral ligand comprising contacting a compound of Formula (I):

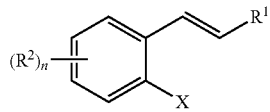

wherein
X is Cl, Br, or I;
R$^1$ is H, alkyl, aryl, heteroaryl, or cycloalkyl;
R$^2$ is H, halo, alkyl, alkoxy, aryl, or heteroaryl; and
n is 0, 1, 2, 3, or 4;
with a hydroborane in the presence of an effective amount of copper(I), a base, and an electron-rich bidentate phosphine ligand, to provide a compound of Formula (II):

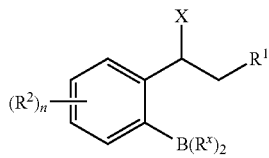

wherein each R$^x$ is independently a boron ligand or both R$^x$ groups together form a bidentate boron ligand;
contacting the compound of Formula (II) with an excess of ammonia or an ammonia equivalent; and converting the boronate to a diphenylphospine moiety to provide a chiral ligand of Formula (II-A):

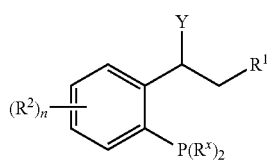

wherein Y is amino and R$^x$ is phenyl.

13. The method of claim 12, wherein the chiral phosphine ligand is (S,S)-Ph-BPE and the chiral ligand is provided in an enantiomeric excess of greater than 90%.

14. The method of claim 13, wherein the compound of Formula (I) is:

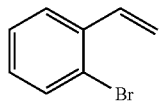

and the product of the reaction is:

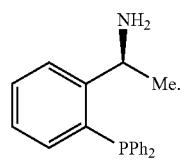

15. The method of claim 12, wherein the compound of Formula (I) is:

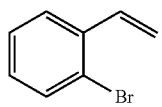

and the product of the reaction is:

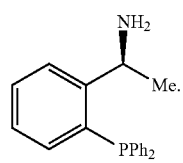

16. The method of claim 12, wherein the copper(I) is formed from CuCl, and the base is an alkali metal alkoxide.

17. A method for preparing a chiral ligand comprising contacting a compound of Formula (III):

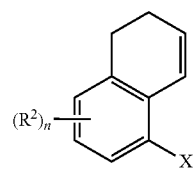

(III)

wherein
 X is Cl, Br, or I;
 $R^2$ is H, halo, alkyl, alkoxy, aryl, or heteroaryl; and
 n is 0, 1, 2, or 3;
with a hydroborane in the presence of an effective amount of copper(I), a base, and an electron-rich bidentate phosphine ligand, to provide a compound of Formula (IV):

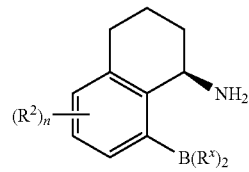

(IV)

wherein each $R^x$ is independently a boron ligand or both $R^x$ groups together form a bidentate boron ligand;
 contacting the compound of Formula (IV) with an excess of ammonia or an ammonia equivalent; and converting the boronate to a diphenylphospine moiety.

18. The method of claim 17, wherein the chiral phosphine ligand is (S,S)-Ph-BPE and the chiral ligand is provided in an ee of greater than 90%.

19. The method of claim 18, wherein the compound of Formula (III) is:

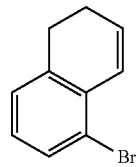 [SMILES: Brc1cccc2c1C=CCC2]

and the compound product of the reaction is:

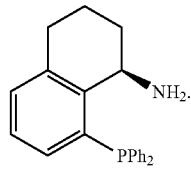

20. The method of claim 17, wherein the compound of Formula (III) is:

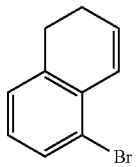 [SMILES: Brc1cccc2c1C=CCC2]

and the compound product of the reaction is:

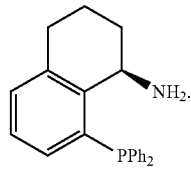

21. The method of claim 17, wherein the copper(I) is formed from CuCl, and the base is an alkali metal alkoxide.

22. A method for preparing a chiral ligand comprising contacting a compound of Formula (V):

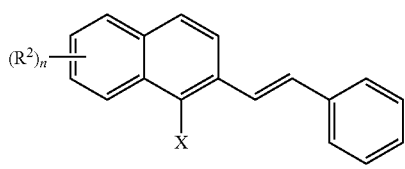
(V)

wherein
X is Cl, Br, or I;
R² is H, halo, alkyl, alkoxy, aryl, or heteroaryl; and
n is 0, 1, 2, or 3;
with a hydroborane in the presence of an effective amount of copper(I), a base, and an electron-rich bidentate phosphine ligand, to provide a compound of Formula (VI):

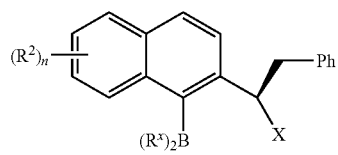
(VI)

wherein each R^x is independently a boron ligand or both R^x groups together form a bidentate boron ligand;
contacting the compound of Formula (VI) with a compound of Formula (VIa):

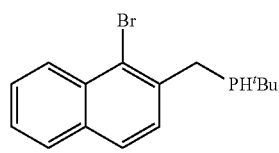
(VIa)

in the presence of an alkyl lithium agent to form a coupled product, oxidizing the coupled product to provide a phosphine, oxidizing the phosphine compound, to provide a phosphine oxide compound, cyclizing the phosphine oxide compound at the bromide and boronate moieties, dimerizing the resulting product in the presence of a strong base, and reducing the phosphine oxide moieties to phosphines, to provide a binapine chiral ligand.

23. The method of claim 22, wherein the chiral phosphine ligand is (S,S)-Ph-BPE and the chiral ligand is provided in an ee of greater than 90%.

24. The method of claim 23, wherein the compound of Formula (V) is:

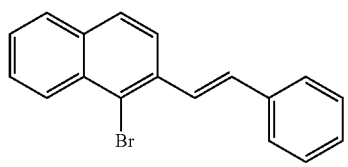 [SMILES: Brc1c(/C=C/c2ccccc2)ccc2ccccc12]

and the compound product of the reaction is:

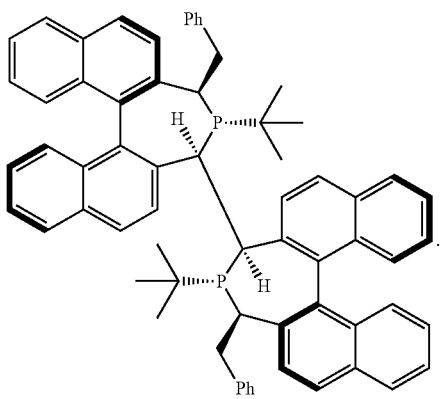

25. The method of claim 22, wherein the compound of Formula (V) is:

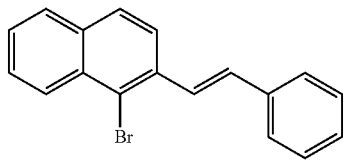 [SMILES: Brc1c(/C=C/c2ccccc2)ccc2ccccc12]

and the compound product of the reaction is:

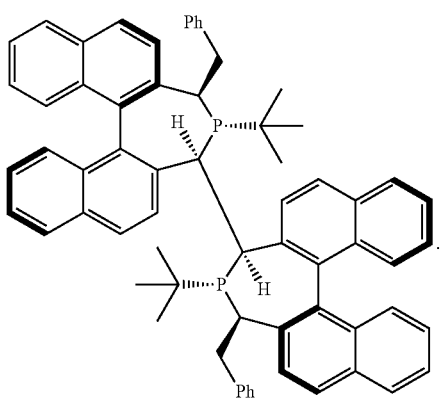

26. The method of claim 22, wherein the copper(I) is formed from CuCl, and the base is an alkali metal alkoxide.

27. A method for preparing a chiral ligand comprising contacting a compound of Formula (I):

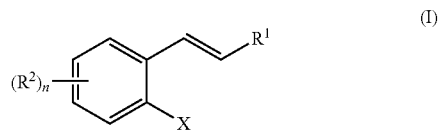
(I)

wherein
X is Cl, Br, or I;
R¹ is H, alkyl, aryl, heteroaryl, or cycloalkyl;
R² is H, halo, alkyl, alkoxy, aryl, or heteroaryl; and
n is 0, 1, 2, or 3;

with a hydroborane in the presence of an effective amount of copper(I), a base, and an electron-rich bidentate phosphine ligand, to provide a compound of Formula (II):

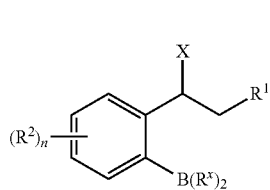

(II)

wherein each $R^x$ is independently a boron ligand or both $R^x$ groups together form a bidentate boron ligand;

contacting the compound of Formula (II) with an excess of tert-butylphosphine oxide in the presence of a strong base to displace the benzylic halide with the tert-butylphosphine oxide, carrying out a hydroformylation reaction in the presence of a Rhodium catalyst followed by cyclization, forming a dimer of the resulting product, and reducing the phosphine oxide moieties to provide a DuanPhos derivative chiral ligand of Formula (VII):

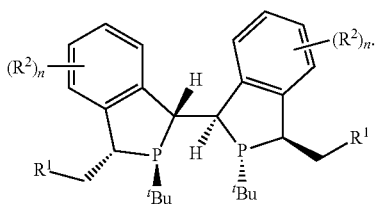

(VII)

28. The method of claim 27, wherein the chiral phosphine ligand is (S,S)-Ph-BPE and the chiral ligand is provided in an enantiomeric excess of greater than 90%.

29. The method of claim 27, wherein the copper(I) is formed from CuCl, and the base is an alkali metal alkoxide.

* * * * *